United States Patent
Van Der Zaag et al.

(10) Patent No.: US 9,493,822 B2
(45) Date of Patent: Nov. 15, 2016

(54) DEVICES AND METHODS FOR MICROARRAY SELECTION

(75) Inventors: Pieter Jan Van Der Zaag, Eindhoven (NL); Harma Feitsma, Eindhoven (NL); Jacob Marinus Jan Den Toonder, Eindhoven (NL); Reinhold Wimberger-Friedl, Eindhoven (NL)

(73) Assignee: KONINKLIJKE PHILIPS ELECTRONICS N.V., Eindhoven (NL)

( * ) Notice: Subject to any disclaimer, the term of this patent is extended or adjusted under 35 U.S.C. 154(b) by 548 days.

(21) Appl. No.: 13/393,255

(22) PCT Filed: Aug. 26, 2010

(86) PCT No.: PCT/IB2010/053839
§ 371 (c)(1),
(2), (4) Date: Feb. 29, 2012

(87) PCT Pub. No.: WO2011/027268
PCT Pub. Date: Mar. 10, 2011

(65) Prior Publication Data
US 2012/0165219 A1    Jun. 28, 2012

(30) Foreign Application Priority Data
Sep. 1, 2009  (EP) .................................. 09169126

(51) Int. Cl.
*C12Q 1/68*  (2006.01)
(52) U.S. Cl.
CPC .................................. *C12Q 1/6834* (2013.01)
(58) Field of Classification Search
None
See application file for complete search history.

(56) References Cited

U.S. PATENT DOCUMENTS

| 5,683,657 A | 11/1997 | Mian | |
| 6,960,437 B2* | 11/2005 | Enzelberger et al. | 435/6.19 |
| 8,323,892 B2 | 12/2012 | Ishibashi et al. | |
| 2003/0008308 A1* | 1/2003 | Enzelberger | B01F 5/102 435/6.19 |
| 2003/0203368 A1* | 10/2003 | Bass | B01J 19/0046 506/7 |
| 2005/0221373 A1 | 10/2005 | Enzelberger | |

(Continued)

FOREIGN PATENT DOCUMENTS

| CN | 2242898 Y | 12/1996 |
| JP | 2003315337 A | 11/2003 |

(Continued)

OTHER PUBLICATIONS

Lipshutz et al., "High density synthetic oligonucleotide arrays", Nature Genetics Supplement, vol. 21, pp. 20-24, (1999).*
Liu et al "Self-Contained, Fully Integrated Biochip for Sample Preparation, Polymerase Chain Reaction Aplification, and DNA Microarray Detection" Anal. Chem. 2004, 76, p. 1824-1831.

(Continued)

*Primary Examiner* — Robert T Crow

(57) ABSTRACT

The present invention relates to a device for the specific selection of target molecules, wherein immobilized capture molecules can be organized in a microarray in the form of spots or lines. In a further aspect the present invention relates to a method of specifically selecting target molecules in a reaction zone, as well as the use of such a device for specifically selecting target molecules, e.g. for target enrichment, or microarray based genome selection (MGS).

8 Claims, 10 Drawing Sheets

(56) References Cited

U.S. PATENT DOCUMENTS

| | | | |
|---|---|---|---|
| 2006/0210984 A1* | 9/2006 | Lambert | B01L 3/5027 435/6.12 |
| 2008/0044821 A1 | 2/2008 | Zainiev | |
| 2008/0194414 A1 | 8/2008 | Albert | |
| 2008/0269073 A1 | 10/2008 | Mirkin | |
| 2009/0087903 A1* | 4/2009 | Belgrader | C12M 41/40 435/303.1 |
| 2009/0325153 A1 | 12/2009 | Shuber | |

FOREIGN PATENT DOCUMENTS

| | | |
|---|---|---|
| JP | 2008134188 A | 6/2008 |
| JP | 2008281381 A | 11/2008 |
| JP | 2009P002913 A | 1/2009 |
| WO | 2005053827 A1 | 6/2005 |
| WO | 2007044071 A2 | 4/2007 |
| WO | 2007122819 A1 | 11/2007 |
| WO | 2008097887 A2 | 8/2008 |
| WO | 2009016770 A1 | 2/2009 |

OTHER PUBLICATIONS

K. Garber "Fixing the Front End" Nature Biotechnology, vol. 26, No. 10, Oct. 2008 p. 1101-1104.

Marguilies et al "Genome Sequencing in Microfabricated High-Density Picolitre Reactors" Nature, vol. 437, Sep. 2005, p. 376-380.

Kawasaki "The End of the Microarray Tower of Babel: Will Universal Standards Lead the Way" Journal of Biomolecular Techniques, vol. 17 p. 200-206, Jul. 2006.

Hodges et al "Genome-Wide in Situ Exon Capture for Selective Resequencing" Nature Genetics, Dec. 2007, p. 903-905.

Albert et al "Direct Selection of Human Genomic Loci by Microarray Hybridization" Nature Methods, Nov. 2007, p. 903-905.

Okou DT, Steinberg KM, Middle C, Cutler DJ, Albert TJ, Zwick "Microarray Based Genomic Selection for High Throughput Resequencing" ME. Nat Methods. Nov. 2007;4(11):907-9.

Wei et al "Comparison of Hybridization Behavior Between Double and Single Strand of Targets and the Application of Asymetric PCR.." Journal of Biochemistry and Molecular Biology, vol. 37, No. 4, Jul. 2004, p. 439-444.

\* cited by examiner

| array | reuse | μg DNA | wash | recovery (μg) | % recovery | unique reads | sequence (Mbp) | on target | on flank | total | 1+cov | 5+cov | 10+cov |
|---|---|---|---|---|---|---|---|---|---|---|---|---|---|
| 1 | 0 | 3 | RT | 3.8E-05 | 0.0211 | 4.8M | 159.5 | 59.2% | 11.9% | 71.1% | 99% | 94.2% | 88% |
| 2 | 0 | 3 | 42°C | 1.4E-06 | 0.0008 | 11.8M | 393.5 | 51.6% | 10.8% | 62.4% | 98.8% | 94.5% | 89.7% |
| 3 | 1 | 1 | RT | 2.3E-06 | 0.0038 | | | | | | | | |
| 4 | 1 | 6.5 | RT | 3.2E-05 | 0.0082 | 13.2M | 443.1 | 65.7% | 12.5% | 78.2% | 99.7% | 98.3% | 96.5% |
| Very low recovery | | | | | | | | | | | | | |

US 9,493,822 B2

DEVICES AND METHODS FOR MICROARRAY SELECTION

FIELD OF THE INVENTION

The present invention relates to a device for the specific selection of target molecules, comprising: (a) at least one reaction zone comprising a microarray, wherein the microarray comprises a substrate, on which one or more species of capture molecules are immobilized, comprising one or more temperature control and/or regulating units for controlling and/or regulating the temperature within the zone; (b) at least one non-reaction zone comprising one or more temperature control and/or regulating units for controlling and/or regulating the temperature within the zone, which is in fluid connection with the reaction zone; and (c) at least one transportation means capable of generating and/or regulating a fluid flow between said reaction zone (a) and said zone comprising one or more temperature control and/or regulating units (b). The present invention further relates to a device for the specific selection of target molecules wherein the immobilized capture molecules are organized in the microarray in the form of spots, elongated spots and/or lines. In a further aspect the present invention relates to a method of specifically selecting target molecules, comprising the introducing a medium to such a device, performing interaction reactions in a reaction zone, transporting not interacted or not bound target molecules to a zone allowing reactivation of the target molecules and performing additional interaction reactions with the reactivated target molecules at the reaction zone, as well as the use of such a device for specifically selecting target molecules, e.g. for target enrichment also referred to as microarray based genome selection (MGS) in the literature.

BACKGROUND OF THE INVENTION

Since the NIH project to initiate the sequencing of the whole human genome at the end of the 1990's, sequencing technology has evolved rapidly. Especially since the introduction of $2^{nd}$ generation of sequencing machines in 2005 the costs of sequencing have been reduced by a factor 10 to around 1 million US $ per human genome at the beginning of 2008. The sequencing industry is now aiming at reducing the costs of DNA sequencing even further with the aim of reaching costs of around 1000 US $ per human genome in the near future. Based on these prospects and expectations, DNA sequencing, in particular the sequencing of genomic DNA, will become a crucial clinical and diagnostic tool, which may be employed for the analysis of genetic variations, the detection of diseases or the elucidation of a predisposition for diseases, in particular for the diagnosis of cancer or the detection of a inclination to develop cancer. The key application of clinical DNA sequencing will, however, not be the sequencing of whole genomes, but rather the re-sequencing of relevant genomic portions or genes known to be involved in the etiology of diseases.

A prerequisite for such an approach is the efficient isolation of target DNA to be sequenced. Typically, complex eukaryotic genomes like the human genome, are too large to be explored without complexity reduction based, e.g., on the direct amplification of specific sequences by PCR methods including short PCR and long PCR, or via fosmid library construction, BAC library construction, TAR cloning or by employing selector technology.

An alternative to the mentioned procedures for reducing the complexity of genomic DNA constitutes the microarray-based genomic selection (MGS), which has been developed to isolate user-defined unique genomic sequences from complex eukaryotic genomes (WO 2008/097887). This method encompasses physical shearing of genomic DNA to create random fragments of an average size of around 300 bp, an end-repairing of the fragments, a ligation to unique adaptors with complementary T nucleotide overhangs and the hybridization of the fragments to a high-density oligonucleotid microarray of complementary sequences indentified from a reference genome sequence, the subsequent elution of the fragments and their amplification via PCR using the adaptor sequences (WO 2008/097887).

However, with current MGS protocols only about 80-90% of the target regions can be recovered. Thus, 10% to 20% of the target sequences are missing and several other regions may be covered only at a low level, which may impede a reliable discovery of mutations in re-sequencing approaches. A hitherto unrecognized problem, which may explain the encountered difficulties to recover the target regions quantitatively is the fact that in typical MGS hybridization mixtures both complementary strands of the genomic DNA are present with high copy numbers, favoring a back-hybridization to the complementary strand instead of a binding to the capture probes.

There is, hence a need for an improved enrichment method for target molecules, in particular target DNA molecules such as genomic nucleic acids, which allows an efficient, reliable and quantitative recovery of the target molecules.

SUMMARY OF THE INVENTION

The present invention addresses this need and provides means and methods for specific selection of target molecules. The above objective is in particular accomplished by a device for the specific selection of target molecules, comprising:

(a) at least one reaction zone comprising a microarray, wherein the microarray comprises a substrate, on which one or more species of capture molecules are immobilized, the reaction zone further comprising one or more temperature control and/or regulating units for controlling and/or regulating the temperature within the reaction zone;

(b) at least one non-reaction zone comprising one or more temperature control and/or regulating units for controlling and/or regulating the temperature within the non-reaction zone, which is in fluid connection with the reaction zone; and (c) at least one transportation means capable of generating and/or regulating a fluid flow between said reaction zone (a) and said non-reaction zone comprising one or more temperature control and/or regulating units (b).

Such a device allows advantageously a repeated reactivation of target molecules which are not bound to the capture molecules, while the area in which target molecules are already bound to capture molecules are kept at a temperature which is ideal for binding. For example, target DNA molecules which are not hybridized to capture probes in an microarray may advantageously be denatured in repetitive cycles, while the area in which the target DNA molecules are bound to the capture probes are kept at an optimal hybridization temperature. Thus, a target molecule, which is not bound to the capture probes, but binds to a complementary target molecule will be reactivated and provided with a further chance of finding a complementary capture molecule, whereas target molecules already bound to capture molecules will remain bound, leading to an enrichment of specifically bound molecules and a significant reduction of target molecules bound to complementary target molecules.

In a preferred embodiment of the present invention the unit for controlling and/or regulating the temperature within the zone may be integrated in the zone, or may be located externally.

In a further embodiment of the present invention the reaction zone (a) as mentioned above, the non-reaction zone comprising one or more temperature control and/or regulating units (b) as mentioned above, and the transportation means (c) as mentioned above are arranged in a closed loop, or in a single flow path or are integrated in a chamber. In a particularly preferred embodiment of the present invention the chamber may be an elongated chamber forming a fluidic channel. In a further preferred embodiment of the present invention the chamber my comprise 2 to 5 repetitions of the reaction zone (a) as mentioned above and the non-reaction zone may comprise one or more temperature control and/or regulating units (b) as mentioned above.

In a further preferred embodiment of the present invention the closed loop or single flow path as mentioned above allows a continuous exchange of fluid between the reaction zone (a) and the non-reaction zone comprising one or more temperature control and/or regulating units (b) as mentioned above.

In a further preferred embodiment of the present invention the device additionally comprises mixing means. Particularly preferred is the presence of the mixing means in regions of fluid connection between the zones.

In a further preferred embodiment of the present invention the non-reaction zone comprising one or more temperature control and/or regulating units (b) as mentioned above or the elongated chamber forming a fluidic channel as mentioned above, comprises a meandering flow path.

In a further, particularly preferred embodiment of the present invention the reaction zone (a) as mentioned above is a hybridizing zone capable of allowing hybridization of nucleic acids to said capture molecules. The device is capable of maintaining the reaction zone at a temperature of about 20° C. to 70° C. Even more preferred is a temperature of about 40° C. to 70° C.

In a further, particularly preferred embodiment of the present invention the zone comprising a temperature control and/or regulating unit (b) as mentioned above is a denaturation zone capable of mediating denaturation of nucleic acids. The device is capable of maintaining the non-reaction zone at a temperature of about 80° C. to 98° C. In an even more preferred embodiment it is kept at a temperature of about 95° C.

In another preferred embodiment of the present invention the immobilized capture molecules are organized in the microarray in the form of spots, elongated spots and/or lines.

In a particularly preferred embodiment of the present invention lines as mentioned above are arranged in an angle of between about 20° and 90°. In a further more preferred embodiment the lines are arranged in an angle of between about 45° and 90°. In yet another, even more preferred embodiment the lines are arranged in an angle of about 90° with respect to the flow path, i.e. the lines are about perpendicular to the flow path.

In another, particularly preferred embodiment of the present invention the lines have a width of between about 300 nm and 30 μm and/or are arranged in an inter-line distance of about 500 nm to 100 μm, with a preferred inter-line distance that is as small as possible. Based on experimental data the area between the lines should preferably be smaller than the area of the lines. Furthermore, the area not covered by probes or probe lines may give rise to a specific binding and thereby lowering the percentage of selected fragments on target In another preferred embodiment of the present invention the capture molecules are molecules selected from the group comprising nucleic acids, peptides, proteins, antigens, antibodies, carbohydrates and/or analogs thereof, preferably nucleic acids. Particulary preferred is the arrangement of the capture molecules on a substrate having a flat surface or being composed of bead-like elements, such as magnetic particles.

In another aspect the present invention relates to a method of specifically selecting target molecules, comprising the steps of: (a) introducing a medium containing one or more target molecules into a zone of a device as mentioned herein above; (b) performing an interaction reaction between said target molecules and immobilized capture molecules in a reaction zone; (c) transporting not interacted or not bound target molecules to a non-reaction zone comprising one or more temperature control and/or regulating units; (d) reactivating, preferably denaturating, said target molecule in said zone comprising one or more temperature control and/or regulating units; and (e) transporting reactivated, preferably denatured, target molecules to the reaction zone, thus allowing further interaction between said target molecule and immobilized capture molecules according to step (b). An advantage of the method, in particular if nucleic acids are selected, is the avoidance of long hybridization times, since an established movement of the medium and the reactivation of the target molecules significantly increase the efficiency of the interaction reaction in the reaction zone.

In a preferred embodiment of the present invention steps (b) to (e) of a method of specifically selecting target molecules as mentioned herein above, may be repeated. In a further preferred embodiment the repetition may be 2 to 100 times, and/or may be carried out continuously and/or in parallel for a predefined time. In yet another preferred embodiment the repetition may be carried out for 1 min to 72 h or for 5 min to 20 h. Most preferred is to carry out the repetition for 10 min to 2 h.

In another aspect the present invention relates to the use of a device as mentioned herein above for specifically selecting target molecules. In a preferred embodiment of the present invention a device as mentioned herein above may be used for carrying out target enrichment.

DETAILED DESCRIPTION OF EMBODIMENTS

Figures 1, 2:
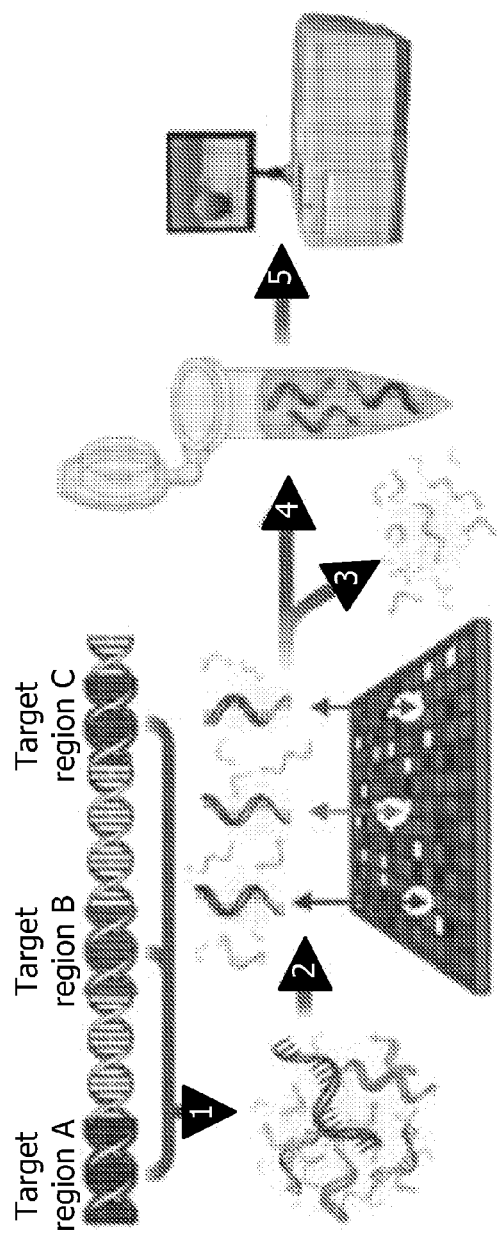
FIG. 1: Schematic illustration of the microarray-based genome selection approach.
FIG. 2: Overview of recovery rates of genomic DNA in a classical microarray-based genome selection carried out with an Agilent array comprising 244.000 different probes to select 0.1% of the human genome; the recovery rate is very low.
Figure 3:
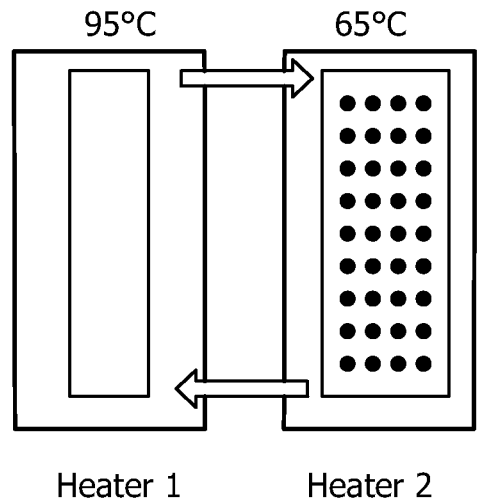
FIG. 3: Schematic representation of a device comprising two chambers, one for hybridization and one for denaturation, between which the fluid is continuously exchanged by closed loop pumping.
Figure 4:
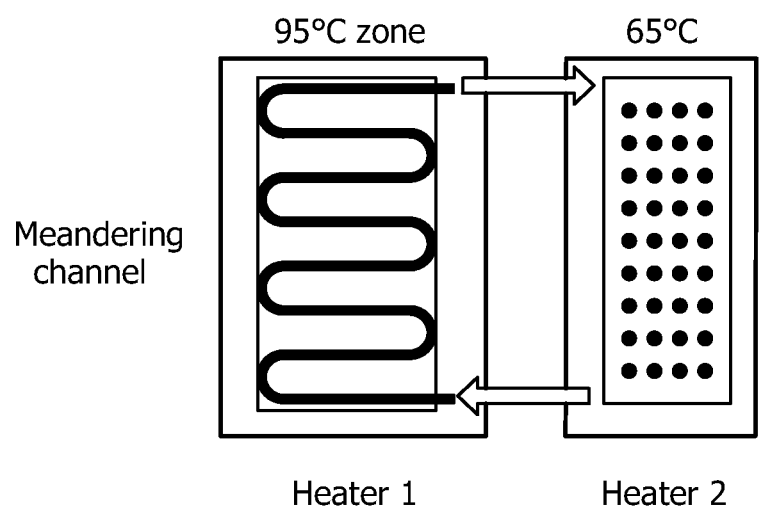
FIG. 4: Schematic representation of a hybridization chamber and a meandering channel which runs over a heated surface and in which the denaturation takes place. The volume, and in particular, the length, determine the residence time of the fluid in the denaturation channel.
Figure 5:
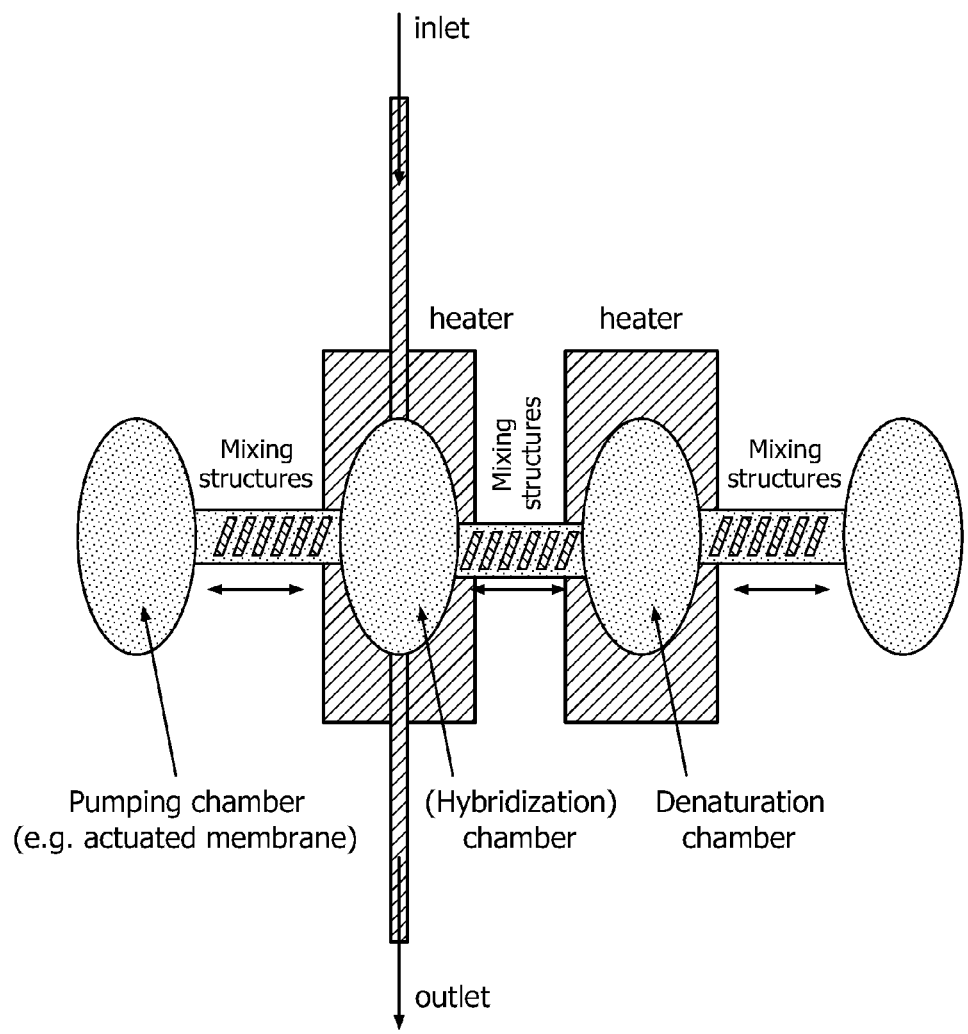
FIG. 5: Schematic representation of a device in which the fluid is pumped back and forth between a denaturation and a hybridization channel. The connecting channels contain passive mixing structures, leading to optimal homogenization of the fluid and its components.
Figure 6A:
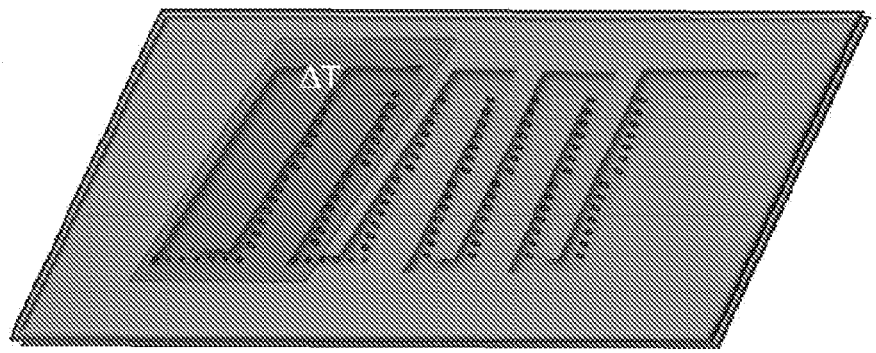
FIG. 6: Schematic representation of a device comprising a meandering channel with different heating zones (FIG. 6A) and a corresponding scheme of the expected and measured fluorescence hybridization intensities (FIG. 6B).
FIG. 6C shows a corresponding scheme of the temperature changes along the channel.
Figure 6B:
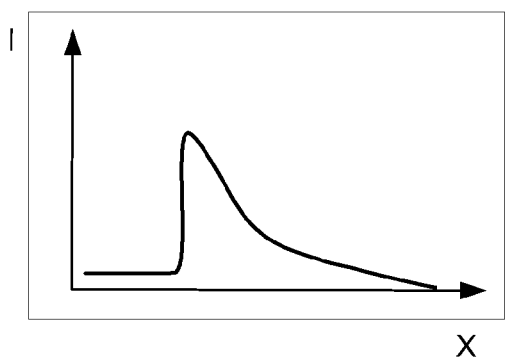
Figure 6C:
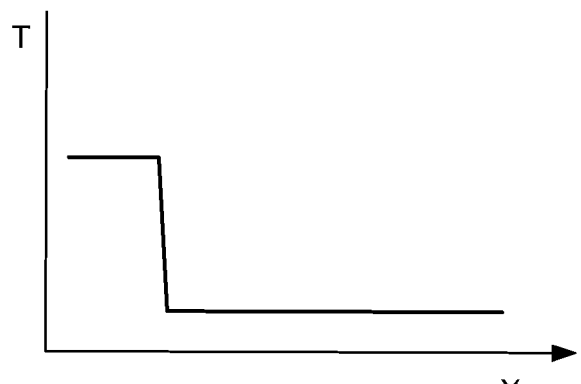

The present invention relates to a device for the specific selection of target molecules as well as corresponding methods and uses.

Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" etc. relate to steps of a method or use there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

As has been set out above, the present invention concerns in one aspect a device for the specific selection of target molecules, comprising: (a) at least one reaction zone comprising a microarray, wherein the microarray comprises a substrate, on which one or more species of capture molecules are immobilized, comprising one or more temperature control and/or regulating units for controlling and/or regulating the temperature within the zone; (b) at least one non-reaction zone comprising one or more temperature control and/or regulating units for controlling and/or regulating the temperature within the non-reaction zone, which is in fluid connection with the reaction zone; and (c) at least one transportation means capable of generating and/or regulating a fluid flow between said reaction zone (a) and said zone comprising one or more temperature control and/or regulating units (b).

The term "selection of target molecules" as used herein refers to the interaction between elements or entities of the device according to the invention and target molecules, e.g. molecules present in the surrounding environment. Such an interaction may be any suitable molecular, sub-molecular or macro-molecular interaction known to the person skilled in the art, e.g. an affinity interaction, an interaction based on van-der-Waals forces, an interaction based on hydrogen-bonding and/or an interaction based on electric charges, e.g. between differently charged molecules. Typical examples of such an interaction would be a protein-protein interaction, a hybridization reaction involving nucleic acids, the binding of a ligand to its receptor, the binding of an antibody to a corresponding antigen or epitope, the binding of a small molecule to the active center of a protein or enzyme, the interaction of a protein or nucleic acid with a carbohydrate structure. Based on the interaction the interacting partner may be bound to one or more elements or entities of the device according to the present invention and thereby selected from the surrounding environment. The selection of target molecules is preferably specific. The term "specific" as used in the context of the selection of target molecules has different meanings, which largely depend on the identity of the target molecule and/or the interaction type and which follow in general suitable rules and definitions known in the art. For example, a nucleic acid-nucleic acid interaction may be considered to be specific if nucleic acid target molecules may interact which are entirely or partially complementary to each other or which are at least about 60% to 99% complementary to each other over their entire length or a portion of the entire length. An interaction between an antibody and its antigen may be considered to be specific according to known standards in the art, e.g. if only the molecular and/or spatial parameters of an epitope may be recognized. An interaction between a ligand and its receptor may be considered as specific according to known standards in the art, for example if a ligand is capable of binding to the receptor's binding area and/or if the ligand is able to convey a molecular reaction in or with the receptor, e.g. the generation of a down-stream signal.

A "target molecule" as used herein may be any suitable molecule, which allows a specific interaction as described herein above. Examples of target molecules to be selected with a device of the present invention are nucleic acids, proteins, peptides, ligands of any form and format, antibodies, antigens, small molecules like organic, inorganic or mixtures of organic and inorganic structures, e.g. carbohydrates or sugars, polymers, entities like cells or cell fragments or cell sub-portions, e.g. bacterial cells, or fragments thereof, eukaryotic cells or fragments thereof, viral particles or viruses, or any derivative or combination of the aforementioned.

The term "surrounding environment" as used herein refers to the material or medium in which the interaction as mentioned above takes place. The medium may, for example, be a fluid medium, a gaseous medium. Preferred is a fluid medium, particularly preferred an aqueous medium, e.g. a medium comprising water in different proportions. In addition the medium may comprise further ingredients, e.g. salts, ions, organic or inorganic molecules, it may be buffered with any suitable buffer known to the person skilled in the art, it may comprise dyes or fluorescent labels, stabilizing agents for nucleic acids or proteins, e.g. RNAse inhibitors, DNAse inhibitors, proteinase inhibitors, it may comprise further interacting elements, e.g. secondary antibodies etc.

The term "reaction zone" as used herein refers to a portion of the device which is suitable for allowing an interaction as mentioned herein above. To be suitable for allowing an interaction one or more parameters may be set or adjusted in a reaction zone. For example, the temperature in a reaction zone may be adjusted to a suitable value known to the person skilled in the art. The value may largely depend on the target molecule to be selected and the interaction type taking place and may differ if a nucleic acid is to be selected or a protein is to be selected or an organic or inorganic small molecule is to be selected etc. Optimal temperatures for such interactions may be derived from a suitable text books e.g. from Lottspeich, F., and Zorbas H. (1998) Bioanalytik, Spektrum Akademischer Verlag, Heidelberg/Berlin, Germany or may be determined experimentally by repeating the reactions at different temperatures, e.g. at temperatures between 4° C. and 120° C., preferably in a range of between about 20° C. and 100° C. A further parameter which may be set or adjusted in a reaction zone according to the present invention, in particular in liquid environments, is the pH, which may be between 0 and 14, e.g. at 0, 1, 2, 3, 4, 5, 6, 7, 8, 9, 10, 11, 12, 13, 14. Preferred is a pH of between about 6.5 and 8.5, more preferred a pH of about 7.5. Another parameter, which may be set or adjusted in the reaction chamber, is the flow rate, in particular the mass flow rate of surrounding material. The mass flow rate may, for example, be between about 0 and 1000 μg/sec, e.g. at 0, 5, 10, 50, 100, 150, 500, 700, 750, 800 or 1000 μg/sec. A further parameter, which may be adjusted or set in a reaction chamber according to the present invention is the overall salt or ionic concentration.

According to the present invention any suitable overall salt or ionic concentration known to the person skilled in the art may be used. For example, the overall salt or ionic concentration may be between about 0.1 mM and 1 M. Any parameter may be present uniformly across the reaction zone or may be present in the form of one or more gradients. For example, there may be a temperature gradient, a pH gradient, a salt concentration gradient and/or a flow velocity or mass flow gradient across the reaction zone. If more than one gradient is present, the gradients may have identical directions or be opposed to each other or be, alternatively, in different directions, e.g. perpendicular or have certain angles, e.g. 30°, 45°, 60° to each other. The parameters may further be changed or modified actively, e.g. during the course of the use of the device, e.g. the temperature may increased or decreased for a certain period of time, the pH may be increased or decreased for a certain period of time and/or the flow velocity or mass flow rate may be increased or decreased for a certain period of time. The reaction zone may be either closed, i.e. comprise a cap, cover or lid, or be open. The reaction zone may be constituted of any suitable material known to the person skilled in the art, e.g. metal, glass, plastics, e.g. PMMA or any derivative or combination thereof. Particularly preferred is the use of glass and/or plastics, e.g. polymeric materials. For the heating/cooling elements metallic materials may be used.

The reaction zone may further comprise a microarray. The term "microarray" as used herein refers to an ordered array presented for interaction between capture molecules in the array and potential interactors in the surrounding environment, e.g. a medium as described herein above. An array may include any two- or three-dimensional arrangement of addressable regions, preferably a two-dimensional arrangement.

A "capture molecule" as used herein may be any suitable molecule, which allows a specific interaction with a target molecule form the environment or the medium in the device according to the present invention as defined herein above. Examples of capture molecules which are capable of selecting target molecules form the environment or the medium in the device are nucleic acids, proteins, peptides, ligands of any form and format, receptors, antibodies, antigens, organic and inorganic structures, e.g. carbohydrates or sugars, polymers, entities like cells or cell fragments or cell sub-portions, e.g. bacterial cells, or fragments thereof, eukaryotic cells or fragments thereof, viral particles or viruses, or any derivative, analog or combination of the aforementioned. Particularly preferred are capture molecules selected from nucleic acids, peptides, proteins, antigens, antibodies and carbohydrates. Even more preferred are capture molecules being nucleic acids.

The term "nucleic acid" as used herein refers to any nucleic acid known to the person skilled in the art, preferably to DNA, RNA, PNA, CNA, HNA, LNA or ANA. The DNA may be in the form of, e.g. A-DNA, B-DNA or Z-DNA. The RNA may be in the form of, e.g. p-RNA, i.e. pyranosyl-RNA or structurally modified forms like hairpin RNA or a stem-loop RNA. The term "PNA" relates to a peptide nucleic acid, i.e. an artificially synthesized polymer similar to DNA or RNA which is used in biological research and medical treatments, but which is not known to occur naturally. The PNA backbone is typically composed of repeating N-(2-aminoethyl)-glycine units linked by peptide bonds. The various purine and pyrimidine bases are linked to the backbone by methylene carbonyl bonds. PNAs are generally depicted like peptides, with the N-terminus at the first (left) position and the C-terminus at the right. The term "CNA" relates to an aminocyclohexylethane acid nucleic acid. Furthermore, the term relates to a cyclopentane nucleic acid, i.e. a nucleic acid molecule comprising for example 2'-deoxycarbaguanosine.

The term "HNA" relates to hexitol nucleic acids, i.e. DNA analogues which are built up from standard nucleobases and a phosphorylated 1,5-anhydrohexitol backbone. The term "LNA" relates to locked nucleic acids. Typically, a locked nucleic acid is a modified and thus inaccessible RNA nucleotide. The ribose moiety of an LNA nucleotide may be modified with an extra bridge connecting the 2' and 4' carbons. Such a bridge locks the ribose in a 3'-endo structural conformation. The locked ribose conformation enhances base stacking and backbone pre-organization. This may significantly increase the thermal stability, i.e. melting temperature of the oligonucleotide. The term "ANA" relates to arabinoic nucleic acids or derivatives thereof. A preferred ANA derivative in the context of the present invention is a 2'-deoxy-2'-fluoro-beta-D-arabinonucleoside (2'F-ANA). In a further preferred embodiment nucleic acid molecules may comprise a combination of any one of DNA, RNA, PNA, CNA, HNA, LNA and ANA. Particularly preferred are mixtures of LNA nucleotides with DNA or RNA bases. In a further preferred embodiment the nucleic acid molecules as defined herein above may be in the form of short oligonucleotides, long oligonucleotides or polynucleotides.

Array elements may be comprised on a substrate. Typically, the array elements or capture molecules are immobilized on the substrate. The term "immobilized" as used herein refers to the association of one or more capture molecules to a supportive substrate via molecular interactions which position the molecule at a specific area of the substrate and concomitantly impede a detaching of the capture molecule, e.g. during washing, rinsing or interaction steps etc. Typically, such molecular interactions are based on covalent chemical bonds between structural elements or functional groups of the support material and the capture molecule to be immobilized, e.g. corresponding functional groups of nucleic acids, as known to the person skilled in the art. The immobilization may, for example, be carried out by crosslinking the capture molecules by heat or light, i.e. by forming molecular interactions or bonds that link both structural elements together under the influence or driven by the energy provided by an energy source like heat or light, or via a chemical immobilization.

Typically, an immobilization via crosslinking by heat is carried out via drying and subsequent baking of capture molecules on a substrate at certain temperatures. Drying and baking are believed to result in molecules becoming attached to the substrate by hydrophobic interaction. This procedure can be classified as a sub-form of physical adsorption. The term "physical adsorption" relates to a process involving initial separation and attraction steps, whereby the capture molecule comes into proximity with the reactive groups, which are based on physical adsorptive processes. The adsorption of a biomolecule, e.g. a nucleic acid, onto a solid support may take place with practically any support material, since it has been observed that any such support material will interact with almost any surface. Typically, the level of interaction between support material and capture molecules to be immobilized varies depending on the nature and form of the support material and the size and chemical properties of the capture molecules. The interaction is typically a five-stage procedure, comprising the steps of (i) transport of the capture molecule to the surface, (ii) adsorption to the surface, (iii) rearrangement of the adsorbed capture molecule, (iv) potential desorption of the adsorbed capture molecule and (v) transport of the desorbed capture molecule away from the surface. Although the procedure implies, to a certain extent, that the potential for desorption is inherent, the binding is typically irreversible, depending on size of the capture molecule. The term "size of the capture molecule" within the context of adsorption interactions relates to the number of binding sites that are present. Although any one binding site may, in principle, dissociate from the surface of the substrate at any time, the effect of a large number of binding sites is that the capture molecule as a whole will remain bound. By applying energy in the form of heat, e.g. at a temperature of about 40 to 150° C., preferably 50 to 120° C., more preferably 60 to 110° C., even more preferably 70 to 100° C. and most preferably 80 to 90° C., the physical adsorption of the capture molecule to the support material may be enhanced and the time necessary for an efficient immobilization may be shortened. The crosslinking by heat may be carried out for any suitable period of time known to the person skilled in the art, e.g. 2 min to 12 hours, preferably 10 min to 8 hours, more preferably 30 min to 6 hours, even more preferably 45 min to 4 hours even more preferably 1 hour to 3 hours and most preferably for 2 hours. The crosslinking by heat or baking may be carried out by any suitable means known to the person skilled in the art, for example a drying chamber or an oven. In addition to the temperature, also other parameters like humidity, aeration or ventilation may be adjusted to suitable values known to the person skilled in the art. The crosslinking by heat or baking may also be combined with other forms of immobilization like crosslinking by light or chemical immobilization.

Crosslinking by light is typically performed by applying light of a typical wavelength, e.g. in a range of 150 to 550 nm, preferably in a range of 200 to 500 nm to capture molecules in order to induce an interaction between the capture molecules and support material. Typically, the induced interaction between the capture molecules and the support material is a covalent binding of the nucleic acid to the material. Crosslinking by light may, for example, be carried out by using UV light. UV crosslinking is one of the simplest ways to ensure covalent binding of a support material to a probe. In the case of nucleic acids, the linkage proceeds through the bases of a nucleic acid molecule, e.g. thymine, guanine, adenine, cytosine or uracil residues, which react with corresponding and suitable functional chemical groups on the support material, as known to the person skilled in the art. The presence and number of functional chemical groups on or inside the support material may be controlled and adjusted via suitable chemical activation processes. Such activation processes may, for instance, provide specifically localized functional groups on or within a support material and facilitate a specific interaction between the capture molecules and the material within the context of these localized functional groups. The presence and number of functional group on or inside the support material may also have an influence on the orientation and freedom of the immobilized capture molecules. For example, the presence of a higher number of functional groups may lead to an immobilization at different points within the capture molecule. Furthermore, the presence of corresponding reactive elements within the capture molecule may be used for a control of the orientation of the capture molecule on the support material.

A "chemical immobilization" as mentioned herein may be an interaction between the support material and the capture molecule based on chemical reactions. Such a chemical reaction does typically not rely on the input of energy via heat or light, but can be enhanced by either applying heat, e.g. a certain optimal temperature for a chemical reaction, or light of certain wavelength. For example, a chemical immobilization may take place between functional groups on a support material and corresponding functional elements on the capture molecules. Such corresponding functional elements in the capture molecules may either be as part of the chemical inventory of a molecule, or be additionally introduced. An example of such a functional group is an amine group. Typically, the capture molecule to be immobilized, e.g. a nucleic acid, comprises a functional amine group or is chemically modified in order to comprise a functional amine group. Means and methods for such a chemical modification are known to the person skilled in the art and can, for example, be derived from organic chemistry textbooks like Organische Chemie by Hart et al., 2007, Wiley-Vch or Organische Chemie by Vollhardt et al., 2005, Wiley-Vch. The localization of said functional group within the capture molecule to be immobilized may be used in order to control and shape the binding behavior and/or orientation of the capture molecule, e.g. the functional group may be placed at the end or tail region of the capture molecule or in the centre of the capture molecule. A typical reaction partner for a capture molecule to be immobilized comprises moieties which are capable of binding to such capture molecules, e.g. to nucleic acids such as amine-functionalized nucleic acids. Examples of such support material are aldehyde, epoxy or NHS substrates. Such material is known to the person skilled in the art. Functional groups, which impart a connecting reaction between capture molecules which are chemically reactive by the introduction of an amine group, and a support material are known to the person skilled in the art. An alternative reaction partner for capture molecules to be immobilized may have to be chemically activated, e.g. by the activation of functional groups, available on the support material. The term "activated support material" relates to a material in which interacting or reactive chemical functional groups were established or enabled by chemical modification procedures as known to the person skilled in the art. For example, a substrate comprising carboxyl groups has to be activated before use. Furthermore, there are substrates available that contain functional groups that can react with specific moieties already present in the nucleic acids. Some of these reactions are enhanced by heat or UV. An example are amine groups on the surface of the substrate, which can be bound to specific bases in the DNA.

Alternatively, the capture probes may be synthesized directly on the substrate. Suitable methods for such an approach are known to the person skilled in the art. Examples are manufacture techniques developed by Agilent Inc., Affymetrix Inc., Nimblegen Inc. or Flexgen BV. Typically, lasers and a set of mirrors that specifically activate the spots where nucleotide additions are to take place are used. Such an approach may provide, for example, spot sizes of around 30 µm or larger. Capture probes may accordingly have a length of up to about 80 nucleotides. In a different, also envisaged technique the capture probes may be deposited by using a non-contact inkjet printing process, in which oligo monomers are deposited uniformly onto specially-prepared glass slides. This in situ synthesis process may typically produce 60-mer length oligonucleotide probes, base-by-base, e.g. from digital sequence files.

The "substrate" may be any suitable substrate known to the person skilled in the art. The substrate may have any suitable form or format, e.g. it may be flat, curved, e.g. convexly or concavely curved towards the zone where the interaction takes place, it may be curled or comprise a wavelike format. It may also be organized in round shape structures. Particularly preferred is the organization in the form of bead-like elements, which may, for example, be arranged in an array. The beads may overly a substrate ground or be fixed in the reaction area by connector elements like rods etc. An example of bead-like elements envisaged by the present invention are magnetic particles comprising capture molecules. Alternatively, coated beads as known to the person skilled in the art may be used.

Typically, the substrate is a solid support, i.e. comprising support material which is mainly of non-liquid consistence and thereby allows for an accurate and traceable positioning of the capture molecule on the support material. An example of a substrate is a solid material or a substrate comprising functional chemical groups, e.g. amine groups or amine-functionalized groups. Further examples of a substrate envisaged by the present invention is a porous support material or porous substrate such as nylon, e.g. Nytran N® or Nytran SPC® or Biodyne C®. A further typical support material or substrate type is a non-porous substrate. Preferred among non-porous substrates are glass, poly-L-lysine coated material, nitrocellulose, polystyrene, cyclic olefin copolymers (COCs), cyclic olefin polymers (COPs), polypropylene, polyethylene and polycarbonate. Nitrocellulose membranes are the traditional membranes which are generally used for transfer techniques in the ambit of nucleic acids. Methods to achieve nucleic acid binding to nitrocellulose, usually by means of physical adsorption, are widely known form the prior art. The principal advantages of nitrocellulose are its ready availability and familiarity. The use of nitrocellulose membranes with radioactive methods of signal detection is well established. As an alternative to nitrocellulose membranes nylon may be used as a substrate, in particular for nucleic acid binding, owing to its greater physical strength and binding capacity, and the wider range of available surface chemistries offered, which optimizes nucleic acid attachment. Immobilization on nylon membranes can be performed, for example, via crosslinking by light, in particular UV-crosslinking, or chemical activation. Immobilization on nylon has been demonstrated to be very durable during repeated probe stripping. As bulk material any suitable material known to the person skilled in the art may be used. Typically, glass or polystyrene is used. Polystyrene is a hydrophobic material suitable for binding negatively charged macromolecules because it normally contains few hydrophilic groups. For nucleic acids immobilized on glass slides, it is furthermore known that by increasing the hydrophobicity of the glass surface the DNA immobilization may be increased. Such an enhancement may permit a relatively more densely packed formation. In addition to a coating or surface treatment with poly-L-lysine, bulk material, in particular glass, may be treated by silanation, e.g. with epoxy-silane or amino-silane or by silynation or by a treatment with polyacrylamide. Bulk material may also be covered with or coated with membrane material as mentioned herein above.

A typical microarray may contain multiple spots, features, areas of individual immobilization or areas of individual molecular identity. For example, an array may contain more than 2, 5, 10, 50, 100, 500, 750, 1000, 1500, 3000, 5000, 10,000, 20,000, 40,000, 50,000, 70,000, 100,000, 200,000, 300,000, 400,000, 500,000, 750,000, 800,000, 1,000,000, 1,200.000, 1,500,000, 1,750,000, 2,000,000 or 2,100,000 spots, features or areas of individual immobilization or areas of individual molecular identity. These areas may be comprised in an area of less than about 20 $cm^2$, less than about 10 cm$^2$, less than about 5 cm$^2$, less than about 1 cm$^2$, less than about 1 mm$^2$, less than about 100 μm$^2$.

A microarray may comprise one or more species of capture molecule, i.e. one or more different types of molecule may be present in a microarray such as nucleic acids and proteins, proteins and carbohydrates etc. Alternatively, the term "one or more species" also relates to capture molecules of the same category or having the same form or format, e.g. nucleic acids, but which are not identical or similar in their molecular identity, e.g. the sequence in the case of nucleic acids or proteins. Thus, a microarray may comprise different nucleic acids, or different proteins, or different carbohydrates, or different antibodies, or different ligands etc., or any combination of different nucleic acids and different proteins etc. If capture molecules of a different molecular identity are present on a microarray, these capture molecules may be partially identical or partially similar, i.e. have, in particular in the case of nucleic acids, overlaps in term of sequence or may have no overlap. These capture molecules may comprise any suitable area or percentage of a genome, e.g. between about 0.00001% to about 30% of a genome, such as at least about 0.00001, 0.00005, 0.0001, 0.0005, 0.001, 0.005, 0.01, 0.02, 0.05, 0.06, 0.07, 0.08, 0.09, 0.1, 0.11, 0.12, 0.13, 0.14, 0.15, 0.16, 0.2, 0.3, 0.4, 0.5, 0.75, 0.8, 0.9, 1, 1.5, 2, 3, 4, 5, 10, 15, 20, or 30% of the genome of an organism, preferably of a mammal genome, more preferably of the human genome and/or be complementary to such regions. Such an area or percentage may comprise, for example, a group of about 2 to 5,000 genes, e.g. 2, 3, 4, 5, 6, 7, 8, 9, 10, 15, 20, 25, 30, 50, 100, 150, 200, 350, 500, 750, 1000, 1200, 1500, 2000, 2500, 3000, 4000, 5000 or more than 5000 genes. Such genes may either be localized in adjacent genomic areas o regions or my alternatively be dispersed throughout the genome. Also sub-groupings, combinations, pattern, e.g. pattern derived from expression data etc. of genes are envisaged.

The reaction zone may further comprise one or more temperature control and/or regulating units. The term "temperature control and/or regulating unit" as used herein refers to a mechanical, electrical (resistive), radiation, microwave, or any other suitable heating device or element, which is capable of providing and/or keeping a temperature in the range of between about 0.5° C. and 120° C., preferably in the range of between about 20° C. and 100° C., more preferably in the range of between about 35° C. and 95° C. The temperature control and/or regulating unit may, thus, function either as heater, if the environmental temperature in the reaction zone is below a certain predefined value or as cooler if the environmental temperature in the reaction zone is above a certain predefined value. The temperature control and/or regulating unit may accordingly comprise a sensor for measuring the environmental temperature and an element allowing the initiation of cooling or heating activity if the measured temperature is not at the predefined value. A predefined value may be any suitable value, preferably a temperature value of between about 0.5° C. and 120° C., preferably in the range of between about 20° C. and 100° C., more preferably in the range of between about 35° C. and 95° C. A temperature control and/or regulating unit may be either independently addressable, e.g. via its own interface to the use, or be integrated in a network of similar units or be connected to a regulating electronic device etc. The reaction zone may preferably comprise between one and 15 temperature control and/or regulating units. If there is more than one such unit, their temperature may be different with respect to the other units or may be identical or similar. By setting such units in the reaction zone to different temperatures for example a temperature gradient within the reaction zone may be generated. Preferably, the reaction zone may be set to a temperature which favors the interaction between target molecules to be selected and capture molecules in the reaction zone.

In a specific embodiment of the present invention the reaction zone may be a bulk reaction zone, i.e. a reaction zone comprising the majority of elements of the device, e.g. the microarray etc. Such a reaction zone may, for example, be located in the interior and/or bottom of a device.

A device according to the present invention further comprises at least one non-reaction zone comprising one or more regulating units for the controlling and/or regulating the temperature in the non-reaction zone, as has been described herein above. Thus, the device comprises a second or further zone with heating and/or cooling elements. The reaction zone and the second non-reaction zone may accordingly show different temperatures or similar temperatures or identical temperatures. Preferably, the at least one second non-reaction zone has a different temperature in comparison to the at least one reaction zone. For instance, if the temperature in the at least one reaction zone is set at value x, the temperature in the second non-reaction zone may be set to value x+10, 15, 20, 25, 30, 35, 40, 45, 50, 55, 60, 65, 70, 75 or 85° C. Preferably, the at least one non-reaction zone comprising one or more regulating units for the controlling and/or regulating the temperature in the zone may be set to a temperature which favors the activation and/or reactivation of target molecules to be selected by the capture molecules in the reaction zone.

Additionally or alternatively, such non-reaction zones may comprise units, elements or equipment allowing to change further parameters such as the presence of charged entities, the presence of ions, or may convey mechanical or shearing forces etc. For example, the non-reaction zone(s) may be suited to establish an electric or electrophoretic current, the zone(s) may be suited to provide a specific pH or a specific presence of chemical or physical entities, e.g. the presence of certain acids, salts, solvents etc. and/or the zone(s) may be suited to provide a strong medium movement. Any of the above mentioned additional facilities may also be available in any of the other parts of a device according to the present invention, e.g. in a reaction zone.

In a specific embodiment of the present invention the, at least one, non-reaction zone comprising one or more temperature control and/or regulating units may be a surface reaction zone. The term "surface reaction zone" as used herein refers to a reaction zone as defined herein above, which is located at the outside or surface of a device according to the present invention. The surface reaction zone may preferably not be equipped with a microarray, but be preferably be used for heating and/or reactivation processes.

The at least one reaction zone and the at least one non-reaction zone comprising one or more temperature control and/or regulating units may further be connected. The connection may be a fluid connection, if a fluid medium is comprised in the device. Alternatively, the connection may also be different, e.g. a gaseous connection or a spatial connection etc. The term "connection" as used herein refers to the provision of the possibility of transporting material, e.g. medium as described herein above, from one zone to another. Such a transport may either be passive, or be enhanced or conveyed by means of transportation. The connection between zones of the device may be in the form of tubes, pipes, pipelines or in the form of extensions of one zone to another, e.g. a juxtaposition of zones. Such a juxtaposition of zones may have any suitable format, e.g. the zones may be connected sideways, or one on top of the other or stacked or may form curved structures etc.

A "transportation means" as present in a device according to the present invention may be any suitable element, apparatus or unit, which allows the movement and/or transport of medium from one zone to the other or vice versa, i.e. from the at least one reaction zone to the at least one non-reaction zone comprising one or more temperature control and/or regulating units. An example of such a transportation means is a pump, e.g. a 3-valve pump or a cilia pump. However, any other types or forms of pumps which can be suitably integrated into device according to the present invention are also envisaged. Such a transportation means may be located between a reaction zone and a non-reaction zone comprising one or more temperature control/and or regulating units, and/or may be located at the extremities of a device. Furthermore, a transportation means may be integrated in one or more zones of the device. The transportation means may preferably regulate the flow of fluids in the device. The regulation may be achieved by setting and/or adjusting the flow rate or velocity of the flow to a certain value. Such a value may be set with regard to, and made dependent on, the material to be transported, the temperature used, the target molecules or capture molecules, the type of interaction which takes place between the target molecule and the capture molecule etc. The transportation means may further be used with different intervals of functioning. E.g. the transportation means may be used for certain period of time, e.g. for about 10 sec, 20 sec, 30 sec, 1 min, 2 min, 3 min, 5 min, 7 min, 10 min, 15 min, 30 min, 40 min, 60 min etc., subsequently be switched off for a certain period of time, e.g., e.g. for about 10 sec, 20 sec, 30 sec, 1 min, 2 min, 3 min, 5 min, 7 min, 10 min, 15 min, 30 min, 40 min, 60 min etc, subsequently be switched on again for e.g. for about 10 sec, 20 sec, 30 sec, 1 min, 2 min, 3 min, 5 min, 7 min, 10 min, 15 min, 30 min, 40 min, 60 min etc., and to forth. The intervals may be changed or modified according to the preceding intervals or the stage of interaction reactions, i.e. it may become longer or shorter in subsequent steps. If more than one transportation means is present in a device, either all transportation means may work or only a sub-portion thereof. The number and location of the transportation means which is active, may be determined and set according to the presence and localization of the reaction zone and/or the second zone.

In a specific embodiment of the present invention a device may comprise one reaction zone, one non-reaction zone comprising one or more temperature control and/or regulating units and one transportation means as described herein above. In further, preferred embodiments of the present invention a device may comprise more than one reaction zone and/or more than one non-reaction zone comprising one or more temperature control and/or regulating units and/or more than one transportation means as described herein above. There may, for example, be a series of 2, 3, 4, 5, 6, 7, 8, 9, 10, 11, 12, 13, 14, 15, 20, 25, 30, 35, 40, 50 or more than 50 reaction zones present in a device. Alternatively or additionally, there may be a series of 2, 3, 4, 5, 6, 7, 8, 9, 10, 11, 12, 13, 14, 15, 20, 25, 30, 35, 40, 50 or more than 50 non-reaction zones comprising one or more temperature control and/or regulating units present in a device. Alternatively or additionally, there may be series of 2, 3, 4, 5, 6, 7, 8, 9, 10, 11, 12, 13, 14, 15, 20, 25, 30, 35, 40, 50 or more than 50 transportation means present in a device. Also a combination of several reaction zones and one non-reaction zone comprising one or more temperature control and/or regulating units and one or several transportation means is envisaged by the present invention.

In a further specific embodiment of the present invention a device may comprise at least one bulk reaction zone and at least one surface reaction zone. A device may also comprise more than one, e.g. a series of 2, 3, 4, 5, 6, 7, 8, 9, 10, 11, 12, 13, 14, 15, 20, 25, 30, 35, 40, 50 or more than 50 bulk and surface reaction zones. Alternatively or additionally, there may be series of 2, 3, 4, 5, 6, 7, 8, 9, 10, 11, 12, 13, 14, 15, 20, 25, 30, 35, 40, 50 or more than 50 transportation means present in a device. All these zones may be integrated in a chamber or may placed in individual casings, e.g. connected with connecting elements as described herein above.

If more than one zone of a type is present in a device, the different types of zones may be present in an array like form, i.e. essentially all grouped together. Alternatively, the different zone types, e.g. the reaction zones, may be followed by non-reaction zones comprising one or more temperature control and/or regulating units, and/or by one or more transportation means.

If more than one reaction zone is present, the reaction zones may comprise different microarrays, i.e. microarrays comprising different capture probes. A "different microarray" may be a microarray which is, for example, capable of interacting with a different portion of genomic DNA, or a different set of proteins, antibodies, ligands etc. Interaction capabilities may also be overlapping between microarrays or zones with capture molecules. Differences between capture probes may also be present in one reaction zone or within one microarray. For instance, a specific interaction may be possible only on one side of the array. One to several of such different microarrays or zones with different capture molecules may be combined, e.g. in the form of series. For instance, a certain area of genomic DNA may be covered by consecutive rows, fields or series of different microarrays or capture molecules.

In a further specific embodiment of the present invention a first reaction zone may comprise capture molecules for abundant target molecules, preferably highly abundant target molecules, e.g. abundant nucleic acid molecules. Subsequent reaction zones may comprise capture molecules for less abundant target molecules, thus forming in a preferred embodiment a sequence of reaction zones from high to low abundance. Interspersed between the one ore more reaction zones, e.g. after every, every $2^{nd}$, $3^{rd}$ etc. reaction zone, or at extreme position may be one or more additional non-reaction zones comprising one or more temperature control and/or regulating units and/or one or more transportation means. Such a setup may preferably be used in order to differentially select complex target molecules since the target molecules are supposed to interact better with the capture molecules as the background is decreased with every new reaction zone.

The zones may be arranged in any suitable form or design. For example all zones may arranged in a continuous line, e.g. in a meandering line as describe herein, or may be arranged radially, e.g. with or without connection via the center of the circle, or may be arranged in a 3-dimensional fashion zones being present below or above a central level.

In a preferred embodiment of the present invention the unit for controlling and/or regulating the temperature within a zone may be integrated in the zone. For example, the unit may be present as heating device in the base or ceiling or a wall of the zone. The integration may be such, that the heating device is covered by a structure, e.g. a glass or plastic plate which preferably allows an easy disposal of heat or coldness. Alternatively, the unit may located as a protruding element in a zone and accordingly be able to dissipate heat or coldness directly to the zone. Both forms may also be combined. Furthermore, one or more means for transportation may be integrated in a zone according to the invention, e.g. a reaction zone. The integration may be such that the transportation means is covered by a structure, or is located as a protruding element in a zone.

In a further preferred embodiment of the present invention the unit for controlling and/or regulating the temperature within a zone may be located externally. For example, the unit may located above or below a zone and dissipate heat in the form of conduction, convection, radiation (infrared or microwaves), or in the form of hot or cold air or liquids, in the form of microwaves, by using Peltier elements etc. Furthermore, integrated cooling and/or heating channels through which cold or hot liquid can be flown or massive cooling elements, e.g. of metal, to which a device may be connected can be used. Also envisaged is a coupling with ultrasonic waves, which may be used for heating purposes. The heat may be generated by electrical dissipation in electrical resistor and/or by Peltier elements. The zones may further be located in chambers or rooms being set to a certain temperature. Furthermore, any of the mentioned integrated and externally provided heating or cooling units may be combined in any suitable manner known to the person skilled in the art.

In a further preferred embodiment of the present invention a reaction zone as defined herein above, a non-reaction zone comprising one or more temperature control and/or regulating units as defined herein above and/or a transportation means as defined herein above may be arranged in a closed loop. The term "closed loop" as used herein refers to an arrangement of the mentioned zones and means which allows a unidirectional flow of material, e.g. fluids, from one zone to the next and a corresponding returning of the material to the starting zone. Such an arrangement allows a continuous, recycling movement of material over identical zones, e.g. the one or more reaction zones. The repetition allows in particular to increase the number of interactions between target molecules and capture molecules by repeating the opportunity of proximity between these molecules. The connection may be a connection as defined herein above, e.g. via tubes, pipes, pipelines etc. In such a setup the flow rate in different parts of the device may be adjusted to the necessities. For example, a flow rate may be used which is reduced in the area of interaction, allowing a prolonged interaction window for the target molecules. The closed loop may further have one or more entry and exit points or ports, e.g. 1, 2, 3, 4 or 5 inlets or outlets. In these ports medium comprising target molecules to be bound to capture molecules may be introduced or removed.

In another preferred embodiment of the present invention a reaction zone as defined herein above, a non-reaction zone comprising one or more temperature control and/or regulating units as defined herein above and/or a transportation means as defined herein above may be arranged in a single flow path. The term "single flow path" as used herein refers to a linear arrangement of the zones without the presence of a looping element. In such an arrangement, a reaction zone may be combined at the one hand side with a transportation means, e.g. a pumping zone or chamber and may be connected on the other side with a non-reaction zone comprising one or more temperature control and/or regulating units as defined herein, which in turn is followed by a transportation means, e.g. a pumping zone or chamber. The connection may be a connection as defined herein above, e.g. via tubes, pipes, pipelines etc. The transportation means accordingly allow a transport of material or medium back and forth over the reaction zone and the non-reaction zone comprising one or more temperature control and/or regulating units as defined herein above. Alternatively, the zones may be arranged in any other combination, as long as their linear arrangement is kept. In a further alternative, bifurcated terminal branches comprising transportation means or a zone as defined above may be used.

In another preferred embodiment of the present invention a reaction zone as defined herein above, a non-reaction zone comprising one or more temperature control and/or regulating units as defined herein above and/or a transportation means may be integrated in a single cavity or chamber. Such an integration may provided in the form of a close proximity of a reaction zone as defined herein above, a non-reaction zone comprising one or more temperature control and/or regulating units as defined herein above and/or a transportation means or an extension or fusion of one of the zones by the next. In a particularly preferred embodiment a device according to the present invention comprises a reaction zone comprising a microarray as defined herein above and more than one temperature control and/or regulating units for controlling and/or regulating the temperature, wherein the temperature in said units is set to two or more different values, e.g. values which favor an interaction between a target molecule and a capture molecule and values which favor the activation or reactivation of the target molecules. Transportation means may accordingly be located in wall regions or be placed at the entry or exit points of the chamber. The chamber may also be arranged in the form of a closed system without entry or exit points or with sealable entry and/or exit points which may be closed once the medium has been entered.

Particularly preferred is an elongated cavity or chamber. The term "elongated" as used herein refers to a form of the chamber in which one side of the chamber is longer than the other. The term "longer" as used herein refers to a factor of about 2, 4, 5, 6, 10, 15, 20, 30, 40 or 50 etc. Typically, the chamber may be broader than lower, e.g. by a factor of about 2, 4, 5, 6, 10, 15, 20, 30, 40 or 50. Alternatively, any other form, shape or arrangement of the chamber known to the person skilled in the art is also envisaged by the present invention.

Such a chamber may comprise, in a further particularly preferred embodiment, any suitable number of repetitions of a reaction zone as defined herein above and/or of a non-reaction zone comprising one or more temperature control and/or regulating units as defined herein above and/or of a transportation means as defined herein above. For example, these zones may be present 2, 4, 5, 6, 7, 8, 9, 10, 11, 12, 13, 14, or 15 times.

In a particularly preferred embodiment of the present invention a closed loop or a single flow path as defined herein above may be arranged such that a continuous exchange of material, e.g. fluid, between the at least one reaction zone and the at least one non-reaction zone comprising one or more temperature control and/or regulating units is possible. The term "continuous exchange of material" as used herein refers to a constant flow rate in the mentioned zones. The term also refers to a quantitative exchange of material between the zones, i.e. all or substantially all material, medium or fluid present in one zone may be transported to the next or a different zone. "Substantially all" as used herein refers to at least about 70, 75, 80, 85, 90, 95, 98, 99, 99.5 or 100% of the material. A corresponding exchange of material may be conveyed by the employment of hydrophobic or superhydrophobic materials in the zones or the connecting regions or connecting tubes or pipes etc., the avoidance of local swirls and turbulences in the zones, e.g. by avoiding nooks or corners in the flow path and/or the adjustment of flow rates etc. to a quantitative exchange etc. The exchange of material of fluid may take place one time or several times, e.g. about 2, 3, 4, 5, 6, 7, 8, 9, 10, 11, 12, 13, 14, 15, 20, 30, 40, 50, 100, 200, 500, 1000 or more than 1000 times.

In a further preferred embodiment of the present invention a device as described herein above may further comprise mixing means. The term "mixing means" as used herein refers to a mixing structure, which is typically in the flow path of a material or medium, e.g. in a fluid or liquid flow path and is capable of causing local swirls and/or turbulences. Such mixing structures may be, for example, one or more distributor or separator rods in a flow path, pimples or extrusion in a flow path, the presence of curves in the flow path or any other suitable mechanical or design element known to the person skilled in the art. Alternatively, a mixing may also be provided by pumping or active mixing units, e.g. turbine like units, stirrer units, bubbler units or medium, in particular fluid agitators. The use of these elements may lead to an increased homogeneity in the zone with respect to the temperature of the medium, in particular the fluid, and/or an increased homogeneity with regard to the content of target molecules to be selected.

The mixing means are preferably located in regions of connection between zones of the device, e.g. in zones of fluid connection between the zones. E.g. all fluid connections, or 10%, 20%, 30%, 50%, 70%, 80% or 90% of the connections may comprise such mixing means. The mixing means may be present in the entrance, the middle, the exit, or at any other position of the connection, or throughout the entire connection. For example, the mixing means may fill about 10%, 20%, 30%, 40%, 50%, 60%, 70%, 80% or 90% of the diameter of the connector, e.g. of a tube, pipe or pipeline.

In a further preferred embodiment of the present invention any of the above described zones and/or the entire device may comprise a meandering flow path. The term "meandering path" as used herein refers to a strongly bended and curved flow path, preferably comprising a signification proportion of the area of a zone. For example, the flow path may be bended or curved such that up to 40%, 50%, 60%, 70%, 80%, 90% or 95% of the area of a zone or of the entire device are covered or occupied by the flow path. The flow path may, in a specific embodiment, comprise one or more microarrays or immobilized capture molecules. In further embodiments of the present invention, the meandering flow path may only be present in a reaction zone or only be present in a non-reaction zone comprising one or more temperature control and/or regulating units. Along the meandering flow path transportation means may be located, e.g. in the wall of the device or at any other suitable location. The meandering flow path may further be provided with a bifurcation leading to the generation of an internal loop, which may further be provided with additional transportation means, allowing a repetitive passing of the medium through the meandering flow path.

Bifurcation points or any other places in the device may be provided with any suitable sort of gates, portals or valves. Such elements may be capable of controlling the direction and velocity of the flow of medium. Furthermore, the zones and/or connectors may additionally comprise sieves and/or filters allowing for the removal or detection of elements in the medium. The sieves or filters may be of specific pore size allowing only the path of objects small than the exclusion size. By using such elements, for instance different types of cells, macromolecules like proteins etc. may be separated.

In a further, particularly preferred embodiment of the present invention the device is a device designed for the selection of nucleic acid target molecules. Accordingly, the device may comprise a microarray of nucleic acid capture molecules, which are preferably complementary to target molecules to be selected as defined herein above. Furthermore, the device may comprises one or more reactions zones, which function as hybridization zones between said microarray and said target molecules to be selected. The temperature in said hybridization zone may be kept at any suitable value, e.g. at a temperature of between about 20° C. and 70° C., between about 40° C. to 70° C., or a temperature of about 20, 30, 40, 42, 45, 50, 55, 58, 59, 60, 62, 65, 67 or 70° C. The temperature may be adjusted or set in dependence of one or more parameters of the hybridization reaction, e.g. the length of the capture molecule, the composition of the medium, the concentration of salts or ions, the pH, the flow rate etc. Capture probe molecules may have a length of between about 20 to 150 nucleotides. Particularly preferred are capture molecules having a length of between about 40 to 70 nucleotides, more preferably of about 50 to 60 nucleotides. Generally, shorter capture molecules may require lower hybridization temperatures and longer capture molecules may require higher hybridization temperatures. In a particularly preferred embodiment of the present invention, the hybridization in the reaction zone is a specific hybridization. Furthermore, lower temperatures may be used for reaction buffers containing a considerable fraction of formamide whereas higher temperatures may be used for reaction buffers without formamide.

The term "specific hybridization" as used herein refers to the binding, duplexing or hybridizing of a nucleic acid to a particular further nucleic acid, e.g. a capture probe, under stringent conditions. The term "stringent condition" in the context of nucleic acid hybridization is sequence and sequence-length dependent, and may be different under different experimental parameters, as the person skilled in the art would know. Examples, of stringent hybridization conditions which may be employed in the context of the present invention are a hybridization in a buffer comprising 50% formamide, 5×SSC, and 1% SDS at 42° C., or a hybridization in a buffer comprising 5×SSC and 1% SDS at 65° C. Exemplary stringent hybridization conditions can also include a hybridization in a buffer of 40% formamide, 1 M NaCl, and 1% SDS at 37° C. Alternatively, a hybridization may be carried out in 0.5 M NaHPO, 4.7% SDS, 1 mM EDTA at 65° C. Further additional stringent hybridization conditions include hybridization at 60° C. or higher and 3×SSC (450 mM sodium chloride/45 mM sodium citrate) or incubation at 42° C. in a solution containing 30% formamide, 1 M NaCl, 0.5% sodium sarcosine, 50 mM MES, pH 6.5. Wash conditions to be used in the context of the present invention may include, for example, a salt concentration of about 0.02 molar at pH 7 and a temperature of at least about 50° C. or about 55° C. to about 60° C.; or, a salt concentration of about 0.15 M NaCl at 72° C. for about 15 mins; or, a salt concentration of about 0.2×SSC at a temperature of at least about 50° C. or about 55° C. to about 60° C. for about 15 to about 20 mins; or, the hybridization complex is washed twice with a solution with a salt concentration of about 2×SSC containing 0.1% SDS at room temperature for 15 mins and then washed twice by 0.1×SSC containing 0.1% SDS at 68° C. for 15 mins; or, equivalent conditions). Alternativly, washing may be carried out in 0.1×SSC/0.1%

SDS at 68° C. Stringent conditions for washing can also be, for example, 0.2×SSC/0.1% SDS at 42° C. Furthermore, any suitable commercially available hybridization and/or washing and/or incubation buffer or medium etc. may be used.

A medium used for hybridization reactions according to the present invention may further comprise specific salts, e.g. salts of carboxyl groups, or acid addition salts of amino groups of molecules. Salts of a carboxyl group may be formed by methods known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. In a further preferred embodiment of the present invention the non-reaction zone comprising a temperature control and/or regulating unit is a denaturation zone. The term "denaturation zone" as used herein refers to the reactivation or denaturation of target molecules to be selected or target molecules to be bound by capture molecules according to the present invention. Preferably, the term relates to a zone capable of and used for the denaturation of nucleic acids. The term "denaturation" as used herein refers to the separation of a double stranded nucleic acid into two single strands, which may occurs when the hydrogen bonds between the strands are broken. In order to allow a denaturation of nucleic acids, the denaturation zone may be kept at a temperature of about 75° C. to 100° C., preferably at a temperature of about 80° to 95° C., e.g. at a temperature of about 80, 82, 84, 85, 86, 87, 88, 89, 90, 91, 92, 93, 94, 95, 96, 97 or 98° C. Particularly preferred is a denaturation temperature of 95° C.

If more than one reaction zone and/or denaturation zone is present in a device according to the present invention, the reaction zones may have individually different temperatures and/or the denaturation zones may have individually different temperatures. Alternatively, all denaturation zones and all reaction zones may have identical or similar temperatures. If capture molecules of different lengths are used in e.g. more than one microarray in the device, the hybridization temperature may be adjusted accordingly, in particular according to the above provided general approach. Conversely, the form, e.g. length and complexity of the target molecules to be selected, i.e. of the nucleic acids may have an influence on the hybridization temperature and/or the denaturation temperature. Both may be decreased with decreasing length of these molecules.

In a further aspect the present invention relates to a novel, improved layout for an array. Such a layout may be used for any type of array, e.g. for microarrays comprising nucleic acids, protein arrays or any other suitable array form, e.g. as described herein above or known to the person skilled in the art. Particularly preferred is an improved layout system to be used or usable in the context of the herein above characterized device(s). Typically, the novel layout for arrays no longer comprises probes to be immobilized in the form of individual locations, but instead provides an organization of these probes in lines. This novel organization of material or elements in an array provides the advantage of increasing the chance that interactors, e.g. complementary nucleic acid molecules, antibodies, ligand etc. find the corresponding capture probe, if compared to the use of spots or other hitherto employed layout forms. The presence of lines crossing the flow path of sample material will further provide the advantage of forcing the sample to cross each probe line at least at some point. Accordingly, the lines may be used as trapping device in order to provide a more efficient interaction between the capture molecules and interacting molecules, e.g. target molecules. The presence of the novel layout comprising lines offers the additional advantage that it is highly usable for selection processes based on microarray technology, since here no subsequent optical detection is necessary, i.e. the optimization of the binding reactions via the presence of lines may be carried out independent of any considerations with respect to the optical detection of interacting elements, i.e. the organization of the array is advantageously dictated only by binding efficiency considerations, but not by considerations concerning the subsequent detection and, more importantly, the distinction of interactions between target molecules and capture molecules.

In a particular embodiment of this novel aspect the array layout may comprise lines, which are provided in an angle of about 5° to about 90° with respect to the flow path over the array.

In a further, particular embodiment of this novel aspect the array layout may comprise lines, which have an angle of about 45° to about 90° with respect to the flow path over the array.

In a further, even more preferred embodiment of this novel aspect the array layout may comprise lines, which are essentially perpendicular or orthogonal with respect to the flow path over the array. The term "essentially perpendicular" as used herein refers to an angle of about 85° to 95, preferably of about 90° with respect to the flow path over the array.

The "flow path" as used in the context of the array layout refers to the stream of material, e.g. a liquid or probes in a liquid, with respect to an array. The flow path may be determined with regard to a device comprising an array in a fixed position, or the array may be arranged with respect to a flow path, by changing its position and/or inclination in the 3-dimensional space. The direction of the flow path over the array may be in any suitable direction, e.g. the flow path may start from any side of the array, from any point of the every side of an array, or from any suitable angle, i.e. from 0° to 360°. The flow path may be parallel or in the same plane as the plane of the array (having an inclination of 0°) or may have an inclination with regard to the plane of the array. For example, the flow path may have an inclination of about 1° to about 45°. If having an inclination, the flow path may be directed from above the array towards the array plane. The flow path may also be changed or reversed during the employment of an array, e.g. to the opposite side, in steps of about 1 to 270°, e.g. in steps of about 5°, 10°, 20°, 30°, 45°, 60°, 70°, 80°, 90°, 120°, 145°, 180°, 270° etc.

In case an array has unequally long sides, e.g. has the form of an oblong or rectangle, the flow path may preferably be directed in parallel to the longer sides. In this configuration, more lines with a reduced length may be placed on the array. Alternatively, the flow path may be directed in parallel to the shorter sides. In this configuration, fewer lines with an increased length may be placed on the array.

In another specific embodiment of this novel aspect the array layout may comprise lines of identical or similar length and/or identical or similar width. Alternatively, the array layout may comprise lines of different lengths and/or different widths. The term "different" as used in this context refers to differences of about 10, 20, 30, 40, 50, 60, 70, 80, 90, 100, 150, 200, 300, 400, 500, 750, 1000 or more than 1000% between the shortest and the longest line or between the finest and the thickest line.

Preferably, all lines in an array reach from one side of an array to the opposite side of an array, leaving no uncovered regions in the direction of the flow path. In an alternative embodiment of this aspect of the invention the lines may also be terminated before the sides of an array, e.g. before both sides or only at one side of the array.

In a further embodiment of this novel aspect, the lines may be continued in direction to the corners of an array, e.g. if they are provided in angle <about 90° and> about 5° with regard to the flow path. If such a continuation is envisaged, the lines in the corner may be of a different quality in comparison to the other lines in the array. They may, for example, be thicker than the other lines. Alternatively, they may comprise capture molecules, which show an easier interaction pattern, than the other capture molecules, leading to a similar amount of interaction in the corner zones in comparison to the rest of the array. In a further alternative they could be used the capture readily captured fragments. Such an approach provides the advantage that in the final sequencing experiment an uniform coverage may be achieved.

In a further embodiment of this novel aspect of the invention each line may comprise a different capture molecule. Alternatively, each line may comprise two or more zones comprising or consisting of different capture molecules, e.g. each line may comprise between about 2 and 100 different capture molecules, e.g. 2, 3, 4, 5, 6, 7, 8, 9, 10, 15, 20, 30, 40 or 50 or more than 50 different capture molecules. The individual zones within a line may be arranged linearly. Alternatively, the lines may comprise two or more zones comprising identical capture zones, interspersed by zones comprising different capture molecules.

In a further embodiment of this novel aspect of the invention identical capture molecules may be present in two or more different lines, e.g. every second or third line etc. may comprise in one zone identical capture molecules. Furthermore, more than one line may comprise a certain capture molecule. E.g. a certain capture molecule may be present in 2 to 50 lines, e.g. in 2, 3, 4, 5, 6, 7, 8, 9, 10, 15, 20, 30, 40, 50 or more than 50 lines in an array. These lines may either be localized one besides the other, or may be distributed in any other suitable pattern in the array. E.g. every $2^{nd}$, $3^{rd}$, $4^{th}$, $5^{th}$, $6^{th}$, $7^{th}$, $8^{th}$, $9^{th}$, $10^{th}$, $15^{th}$, $20^{th}$, $30^{th}$, $40^{th}$, $50^{th}$, $100^{th}$ etc. line may comprise or consist of a certain or specific capture molecule.

In a further embodiment of this novel aspect of the present invention the lines as defined herein above may have a width of between about 100 nm to about 100 μm, preferably of about 300 nm to 30 μm, e.g. a width of about 150 nm, 200 nm, 300 nm, 400 nm, 500 nm, 600 nm, 700 nm, 750 nm, 800 nm, 900 nm, 1 μm, 2 μm, 5 μm, 7 μm, 10 μm, 12 μm, 15 μm, 20 μm, 25 μm, 30 μm, 35 μm, 50 μm, 75 μm or 100 μm.

In a further embodiment of this novel aspect of the present invention the lines as defined herein above may be arranged in any suitable and technically feasible interline-distance. The inter-line distance may preferably be as small as possible. As proved by experiments the area between the lines should preferably be smaller than the area of the lines. Furthermore, the area not covered by probes or probe lines may give rise to a specific binding and thereby lowering the percentage of selected fragments on target. The interline-distance may be of about 25 nm to 200 μm, preferably of about 500 nm to about 100 μm, e.g. an inter-line distance of about 600 nm, 700 nm, 750 nm, 800 nm, 900 nm, 1 μm, 2 μm, 5 μm, 7 μm, 10 μm, 12 μm, 15 μm, 20 μm, 25 μm, 30 μm, 35 μm, 50 μm, 75 μm, 100 μm, 150 μm or 200 μm.

In a further embodiment of this novel aspect of the present invention any suitable amount of lines may be generated on an array. The amount of lines may primarily depend on the number and/or length and/or complexity of capture molecules to be placed on the array, the type of array substrate, the envisaged overall size of the array etc. n a predefined, exemplary array area of about 1000 μm², a number of about 2 to 30,000 lines may be placed, preferably a number of 5,000 to 25,000 lines, more preferably a number of 10,000 to 23,000 lines In a further embodiment of this novel aspect of the present invention the lines as defined herein above may be arranged in conjunction with different deposition forms, e.g. with spots, elongated spots, circles of lines, rectangles of lines, spirals etc. Circles of lines, rectangles of lines, spirals or any other curved or connected line form may also be employed as sole layout type. The terms "spots" and "elongated spots" as used herein refers to either disk-like elements or to short, broad lines, respectively.

In case a combination of different deposition forms is used as a layout, the different form elements may either be interspersed, or similar elements may be kept in zones, followed by the next element type etc. Alternatively, the elements may be distributed randomly on the array. Furthermore, the elements may be deposited in dependence of the flow path over an array, e.g. with lines crossing the flow path, spots between the lines or at the boundaries of the flow path etc.

The lines according to this novel aspect of the present invention may be generated with the help of any suitable technique known to the person skilled in the art, e.g. with spotting techniques involving ink jet technology, with dip pen lithography, with laser based growth techniques or micro-contact printing, or with imprint-, or photolithographic technology. Such techniques and their implementation would be known to the person skilled in the art. For instance lithography methods as offered by Affymetrix Inc. may be used.

In a preferred embodiment of the present invention a device as mentioned herein above may comprise immobilized capture probes, which are organized in the form of spots, elongated spots or lines. Particularly preferred is an organization of the capture probes in the form of a layout comprising lines as defined herein above. Furthermore, the immobilized capture probes may be organized in a mixture of different layout forms, preferably a mixture as defined herein above.

In a further preferred embodiment the device according to the present invention may comprise immobilized capture probes, which are arranged in lines being in an angle of between about 20° and 90° with respect to the flow path. Further preferred is in an angle of between about 45° and 90° with respect to the flow path. Particularly preferred is an angle of about 90° with respect to the flow path, i.e. a perpendicular orientation of the lines with regard to the flow path. The lines may further have different angles with respect to the flow path, in particular angles as defined herein above in the context of the array layout aspect.

In a further preferred embodiment the device according to the present invention may comprise lines having a width of between about 300 nm and 30 μm. Preferred is a width of 300 nm. Also preferred are widths of 0.5 μm, 1 μm and 10 μm. Furthermore, the lines may be arranged in an inter-line distance of about 50 nm to 100 μm. Particularly preferred is an inter-line distance of 2 μm. Additionally, the lines may have any widths as defined herein above in the context of the array layout aspect.

In a further aspect the present invention relates to a method of specifically selecting target molecules, comprising the steps of: (a) introducing medium containing one or more target molecules into a zone of any of the devices as defined herein above; (b) performing an interaction reaction between said target molecules and immobilized capture molecules in a reaction zone; (c) transporting not interacted or not bound target molecules to a non-reaction zone comprising one or more temperature control and/or regulating units; (d) reactivating said target molecule in the non-reaction zone comprising one or more temperature control and/or regulating units; and (e) transporting reactivated target molecules to the reaction zone, thus allowing further interaction between the target molecule and immobilized capture molecules according to step (b). The term "medium containing one or more target molecules" as used herein refers to a medium comprising a target molecule as defined herein above, e.g. nucleic acids, proteins, peptides, ligands of any form and format, antibodies, antigens, small molecules like organic, inorganic or mixtures of organic and inorganic structures, e.g. carbohydrates or sugars, polymers, entities like cells or cell fragments or cell sub-portions, e.g. bacterial cells, or fragments thereof, eukaryotic cells or fragments thereof, viral particles or viruses, or any derivative or combination of the aforementioned, which are comprised in a medium. Preferably, the target molecule is a nucleic acid, more preferably DNA, even more preferably genomic DNA, most preferably human genomic DNA.

The nucleic acid, being comprised in the medium, may previously have been processed in order to allow an interaction with capture molecules. Such a processing may include, as a first step, the shearing of nucleic acid molecules, e.g. of genomic DNA. For instance, a physical shearing may be carried out according to suitable procedures known to the person skilled in the art, e.g. derivable from WO 2008/097887. Typical shearing methods include the use of sonication, nebulization or a combination of both. Subsequently, the nucleic acid molecules may be repaired. An exemplary, suitable repairing approach is an end repairing based on blunt end and phosphorylation reactions known to the person skilled in the art. Additionally or alternatively, the nucleic acid molecules may be connected to adaptor molecules, allowing a subsequent amplification reaction. Such adaptor molecules may be ligated to the nucleic acid molecules according to any suitable method known to the person skilled in the art. Such adapators may further prevent or reduce self ligation due to overhangs on the adaptor molecule, may be unique with regard to the target nucleic acids and/or may be complementary to one another (see also WO 2008/097887). After any of the aforementioned steps, the nucleic acids may be cleaned and mixed with a suitable medium. An example of such a medium is a hybridization buffer or solution as defined herein above.

The medium may be introduced into the device according to any suitable technique known to the person skilled in the art. Typically, the medium may be introduced into the device via one or more of the inlets described herein above. Alternatively, a cap may be lifted and the medium may be introduced over the entire area of the device; subsequently the cap may be closed again. The device may also be connected to a network of other devices, e.g. an automated detection apparatus or conjunction of appartuses. Accordingly, the medium may automatically be delivered to the device via introducing tubes or canals, preferably equipped with valves and/or transportation means. The medium may be introduced into any zone of a device according to the present invention. Preferably, the medium is introduced into a non-reaction zone comprising one or more temperature control and/or regulating units for controlling and/or regulating the temperature within the zone. If the medium is introduced into said zone, the medium may, before continuing with the subsequent step, be activated, e.g. by a heating step, e.g. to a temperature of about 80 to 99° C., preferably to 95° C. The medium may subsequently be transported to the reaction chamber, preferably by using a means of transportation as mentioned herein above.

Subsequently, an interaction reaction between the target molecules and the immobilized capture molecules may be carried out. In a specific embodiment of the present invention the interaction is an interaction between nucleic acid molecules. Accordingly, the performance of a hybridization reaction is particularly envisaged by the present invention. Such a hybridization reaction may be carried out according to any suitable protocol known to the person skilled in the art, preferably according to the details provided herein above. Particularly preferred is a hybridization reaction carried out at a temperature of about 40° C. to 70° C. The hybridization may, for instance, be carried out at a temperature of about 40° C., 42° C., 44° C., 45° C., 50° C., 55° C., 60° C., 65° C. etc. As capture molecules any of the above mentioned capture molecules may be used, in the case of nucleic acids capture molecules comprising nucleic acids as defined herein above may be used. An interaction reaction as described may result in an interaction of one or more capture molecules and one or more target molecules, e.g. nucleic acid molecules may bind to complementary capture molecules. The degree of interaction or binding capability between nucleic acid molecules, e.g. between target molecules and capture molecules, may be adjusted via several parameters, e.g. the hybridization temperature, the amount of salts and/or formamide in the buffer, the flow rate in the reaction zone etc. Preferably, a complementartiy of about 80% to 100% may be reached, more preferably a complementarity of 85%, 90%, 95%, 97%, 98% or 99%. Additionally, the result of the interaction process may be controlled, e.g. by using suitable control devices known to the person skilled in the art, e.g. the detection of fluorescence signals etc.

Target molecules which did not interact with capture molecules or which did not bind to the capture molecules, e.g. in the case of nucleic acids those nucleic acids which became double-stranded via an interaction with a further complementary single-stranded nucleic acid, but did not form duplexes with the capture molecule, may subsequently be transported away from the reaction zone. This transport may be performed by transportation means as described herein above. In a specific embodiment, a constant or continuous flow of medium or material is generated in the device, which may lead to an exchange or replacement of medium or material in the reaction zone. The medium or material, e.g. the hybridization buffer comprising the non-bound target molecules or nucleic acids, may arrive at a non-reaction zone comprising one or more temperature and/or regulating units. Such a zone may be spatially separated from the reaction zone, or may be integrated therein as described herein above in the context of the devices of the present invention. The zone may, in a specific embodiment, be set at a temperature which is above the temperature used in the reaction zone.

Upon arriving at a non-reaction zone comprising one or more temperature and/or regulating units, the target molecules may be reactivated. The reactivation may be any suitable process known to the person skilled in the art allowing the generation of the status quo antes, in particular a status allowing the target molecule to interact with the capture molecule. The reaction may depend on the type of target molecule and/or the type of capture molecule used. In the case of nucleic acids, the reactivation may comprise a rise of the temperature leading to a melting of duplex structures, i.e. a denaturation of the nucleic acids. In the case of antibody or ligand interactions, parameters like the temperature, the presence of charged units, the presence of ions, mechanical or shearing forces etc may be changed. For example, an electric current may be established, the pH may be changed, a strong medium movement may be generated etc. Particularly preferred is denaturation of nucleic acid molecules at a temperature of about 80° C. to 98° C., more preferably of about 95° C. The reactivation step may be carried out for any suitable lengths of time and may be controlled, for instance, by the velocity or flow rate in the device. Typically, the flow rate in or close to the non-reaction zone may be reduce, or transportation means may be used non-continuously, e.g. in certain intervals of about 0.1 sec to 10 min, allowing the reactivating process to take place. In the case of nucleic acids, the reactivation or denaturation process may preferably result in a denaturation of about 50% to 100%, more preferably of at least about 70%, more preferably of at least about 85% and most preferably of essentially all double-stranded target molecules. The effects of the reactivation process may further be controlled by suitable controlling mechanisms known to the person skilled in the art, e.g. the use of intercalating molecules, the use of fluorescence detection etc.

Subsequently, the reactivated, e.g. denatured, target molecules may be transported to a reaction zone, where an interaction with the target molecule and the capture molecule may take place. The reaction zone may be the same zone already used in the first interaction scheme, or may be a different zone. For example, if a series of reaction zones, e.g. interspersed by denaturation zones, is used, the reactivated target molecules may be transported to different reaction zones. By using control devices as mentioned above it may further be possible to check the amount of target molecules present in the medium. Depending on the amount of target molecules present in the medium the transport of the medium may, in a specific embodiment of the present invention, be controlled. Typically, the transport may only be carried out as long as at least more than 0.01, 0.1, 0.5, 1, 2, 3, 4, 5, 10, 20, 30, 40 or 50% of the original amount of target molecules is still present in the medium. Is such a threshold not reached, the transporting may be ceased and/or the method may be stopped. Alternatively, if the threshold is not reached, a continuation of the process steps may be envisaged, e.g. by generating a looping of the flow to the first reaction zone or any other the reaction zones. Such a looping may be achieved by employing valves, alternative tubes or pipes etc. of a device as described herein above.

In a specific embodiment of the present invention, any of the above described method steps may be carried out individually or separately from the other steps. Furthermore, one or more of the steps may be cancelled or left out and/or the sequence of steps may be reversed or altered in any suitable way. For instance, after having introduced a medium containing one or more target molecules into a zone of a device, having performed an interaction reaction between said target molecules and immobilized capture molecules in a reaction zone; and having transported not interacted or not bound target molecules to a zone comprising one or more temperature control and/or regulating units the method may be stopped. Alternatively, there may be no transporting step involved and the medium may be reactivated, e.g. denatured, in situ, e.g. in a gradient of temperature. Such a method may be combined with an elution via heat as defined herein below.

In a further preferred embodiment of the present invention the step of performing an interaction reaction, the step of transporting not interacted or not bound target molecule to a zone comprising one or more temperature control and/or regulating units, and the step of reactivating the target molecule in the non-reaction zone comprising one or more temperature control and/or regulating units, and/or the step of transporting reactivated target molecules to the reaction zone may be repeated one to several times. The repetition may be performed, e.g. up to 1000 times, preferably up to 100 times. The steps may further be carried out in a sequential order, i.e. one after the other, or in parallel, in particular if a series of zones is used. The steps may also be carried out continuously, e.g. in a recycling manner. Both variants may also be combined, when necessary.

The method may, in a further specific embodiment, be carried out for any suitable time. For example, the method may be carried out for between about 0.5 min to 150 h, preferably for about 1 min to 72 h, more preferably for about 5 min to 20 h. Even more preferably, the method may be carried out for 10 min to 2 h. The running time may be made dependent, for example, on the type, structure, amount, complexity of the capture molecules and/or the target molecules.

Subsequent to the termination of the transportation, interaction and/or reactivation steps interacted or bound target molecules may be recovered from the microarray according to any suitable procedure known to the person skilled in the art. For example, in the case of nucleic acids, the bound DNA fragments may be eluted from the microarray, e.g. according to protocols mentioned in WO 2008/097887, in particular in Examples 3-13 of said document. Preferred is an elution of nucleic acids based on high temperatures, e.g. temperatures of 90-99° C., e.g. 95° C. In the case of protein or ligand interaction corresponding, suitable recovery or elutation procedures may be used. Such procedure, e.g. the employment of high salt concentrations, high temperature such as 95° C. or the use of NaOH are known to the person skilled in the art and may be derived from textbooks like Lottspeich, F., and Zorbas H. (1998) Bioanalytik, Spektrum Akademischer Verlag, Heidelberg/Berlin, Germany. The accordingly recovered molecules may subsequently be further processed or analyzed. In the case of nucleic acids, the molecules may be further amplified via PCR and/or may directly used for sequencing procedures In a specific embodiment of the present invention an elution based on high temperatures may be carried out with units for controlling and/or regulating the temperature within the zone as defined herein above. For example, the units for controlling and/or regulating the temperature within the zone as defined herein above which are present in a reaction zone may be heated up to temperature of about 95° C. resulting in an elution of the interacted elements, e.g. nucleic acids. Such a step is typically carried out after the initial not targeted molecules, e.g. part of the genomic DNA has been flushed away. These elements may subsequently be recovered by any suitable means, e.g. with the help of transporting means, via reservoirs, receiving units, basins etc. Such an elution may be carried out during the performance of further interaction steps in other zones or during the performance of the entire device or after the termination of parallel assay reactions. Eluted molecules may, in a further embodiment, also be used for a further interaction in the same device, e.g. with the same capture molecules or with a different type of capture molecule or microarray. Such an approach may be used in order to select for two or more different features present in one type of target molecule.

In a further aspect the present invention relates to the use of a device of the present invention for specifically selecting target molecules, in particular target molecules as described herein above. Examples of such target molecules are nucleic acids, proteins, peptides, ligands of any form and format, antibodies, antigens, small molecules like organic, inorganic or mixtures of organic and inorganic structures, e.g. carbohydrates or sugars, polymers, entities like cells or cell fragments or cell sub-portions, e.g. bacterial cells, or fragments thereof, eukaryotic cells or fragments thereof, viral particles or viruses, or any derivative or combination of the aforementioned. Particularly preferred is the use of a device according to the present invention for the selection of nucleic acids, more preferably of DNA molecules, even more preferably of genomic DNA molecules, e.g. human or mammalian genomic DNA molecules. These genomic DNA molecules may be selected according to the presence of complementary regions in the capture molecules. Typically, a portion of a genome may be selected by this approach, e.g. about 0.00001% to about 30% of a genome, such as at least about 0.00001, 0.00005, 0.0001, 0.0005, 0.001, 0.005, 0.01, 0.02, 0.05, 0.06, 0.07, 0.08, 0.09, 0.1, 0.11, 0.12, 0.13, 0.14, 0.15, 0.16, 0.2, 0.3, 0.4, 0.5, 0.75, 0.8, 0.9, 1, 1.5, 2, 3, 4, 5, 10, 15, 20, or 30% of the genome of an organism, preferably of a mammal genome, more preferably of the human genome. Such an area or percentage may comprise, for example, a group of about 2 to 5.000 genes, e.g. 2, 3, 4, 5, 6, 7, 8, 9, 10, 15, 20, 25, 30, 50, 100, 150, 200, 350, 500, 750, 1000, 1200, 1500, 2000, 2500, 3000, 4000, 5000 or more than 5000 genes. Such genes may either be localized in adjacent genomic areas o regions or my alternatively be dispersed throughout the genome. Also sub-groupings, combinations, pattern, e.g. pattern derived from expression data etc. of genes are envisaged. The preprocessing, preparation of the target molecules, the preparation of capture molecules, the elution of molecules, the post-processing etc. may be carried out along suitable procedures known in the art, e.g. according to microarray-based genome selection (MGS) procedures, target capture procedures pre-sequencing enrichment procedures as described in WO 2008/097887. In a particularly preferred embodiment the devices or methods of the present invention may be used for target enrichment, e.g. for carrying out a microarray-based genome selection, target capture, or pre-sequencing enrichment.

The following examples and figures are provided for illustrative purposes. It is thus understood that the example and figures are not to be construed as limiting. The skilled person in the art will clearly be able to envisage further modifications of the principles laid out herein.

EXAMPLES

Example 1

Hybridization of oligonucleotides (ON) on an array of spots with capture ONs on a glass substrate functionalized with amino-silane surface.

Spots of app. 100 micrometer diameter were created by printing oligonucleotide (ON) (19 b) solution in PBS in an array fashion with a pitch of 300 µm. After drying the substrates were illuminated with UV radiation to cross-link the polyA part of the ON to the amino groups present at the surface, followed by a washing step. A cover of glass was placed on the substrates with the aid of a laser cut pressure-sensitive adhesive (PSA) layer. The shape of the PSA was chosen such that a meander-like channel is created which connects two fluid ports on the cover with each other. These devices were placed on a patterned heater device with 6 individually controllable zones of 3×6 mm area and integrated temperature sensors.

Figure 7:
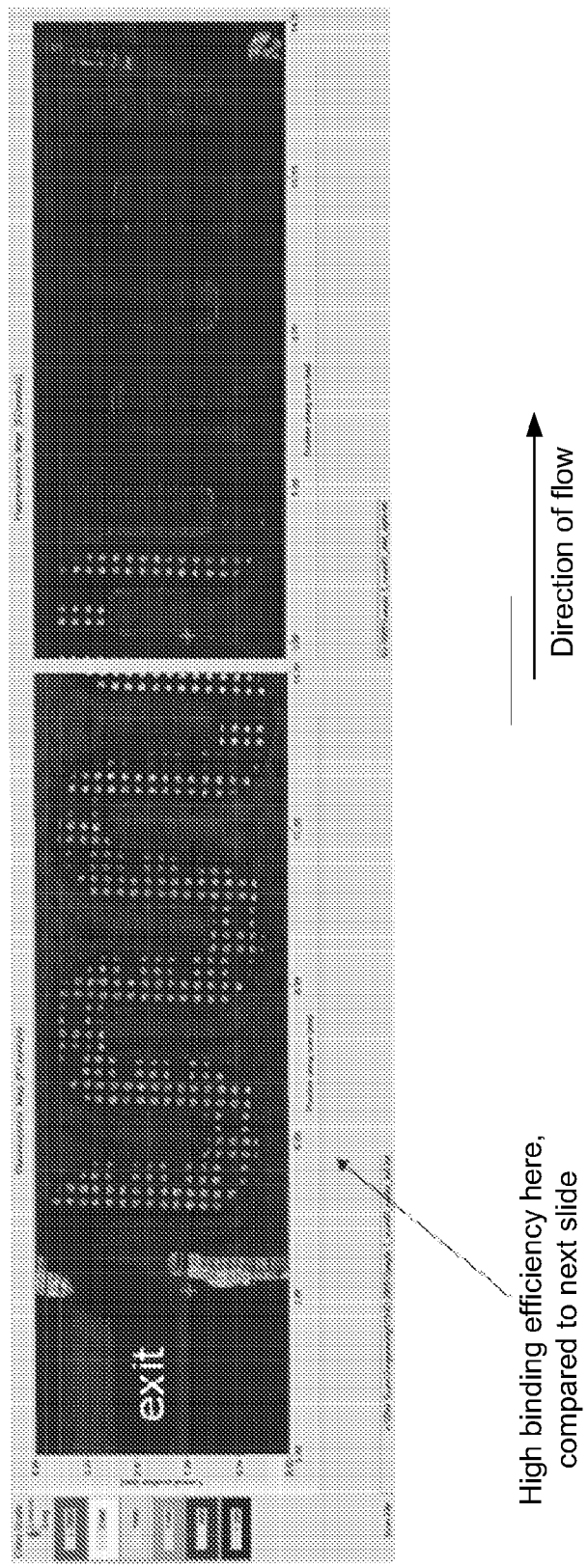
FIG. 7: Image showing a high binding efficiency in the terminal portion of a meandering channel comprising different heating zones set to 95° C. The direction of flow is from right to left, the exit is on the left hand side.

Solutions of single-stranded (ss) and double-stranded (ds) oligonucleotides with complementary sequence to that of the capture probes and equipped with a fluorescent label (Atto 700) with different concentrations were pumped through the meander channel at a rate of 6 µl/min while the device was heated with the 6 heating zones at the following temperature settings: 50/50/95/95/50/50° C. in the direction of flow during 30 min. At the end of this flow-over incubation a washing solution of PBS was pumped through the channels for 5 min at room temperature. After drying the devices were put on a confocal fluorescence scanner and the intensity of the spots was read out. FIG. 7 shows a typical result of the resulting intensities in the meander channel with the direction of flow indicated for the case of a ds ON solution of 10 nM concentration. The fluorescence intensity is very low at the inlet section of the meander but very high at the outlet section, i.e. after passing the 95° C. zone in which the ds ON denatures so that the free ss ON can hybridize to the complementary ON capture probe at the surface.

Figure 8:
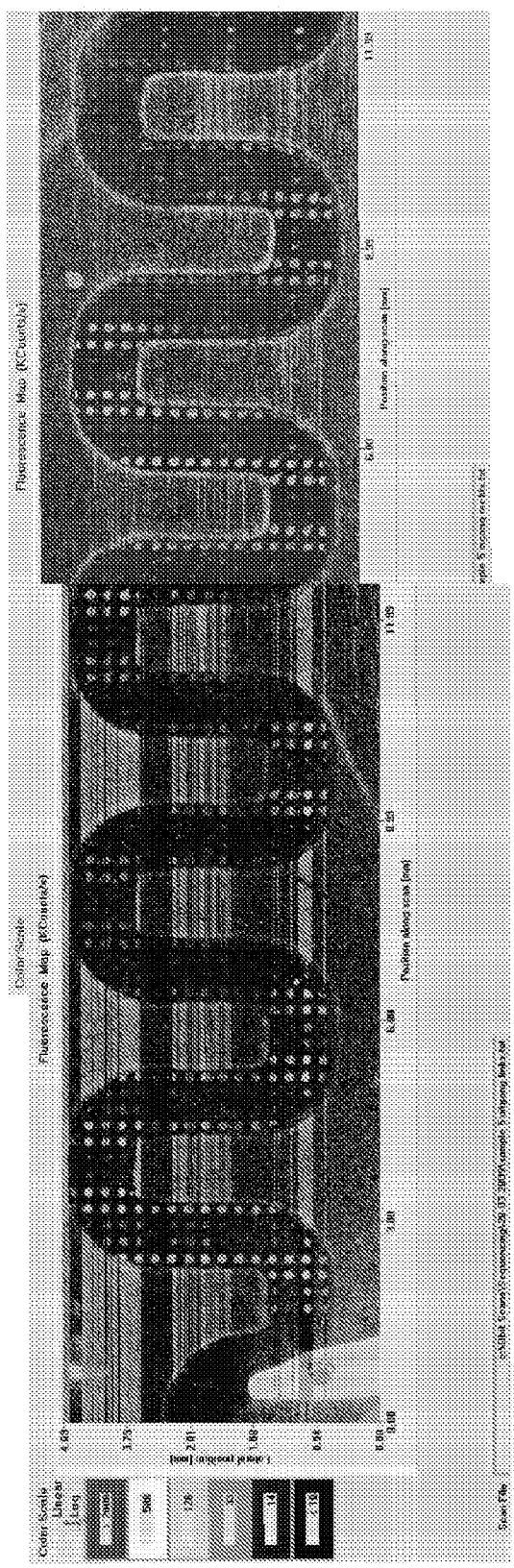
FIG. 8: Image showing a low binding efficiency in the meandering channel, which was set to a temperature of 50° C. The direction of flow is from right to left, the exit is on the left hand side.
Figure 9:
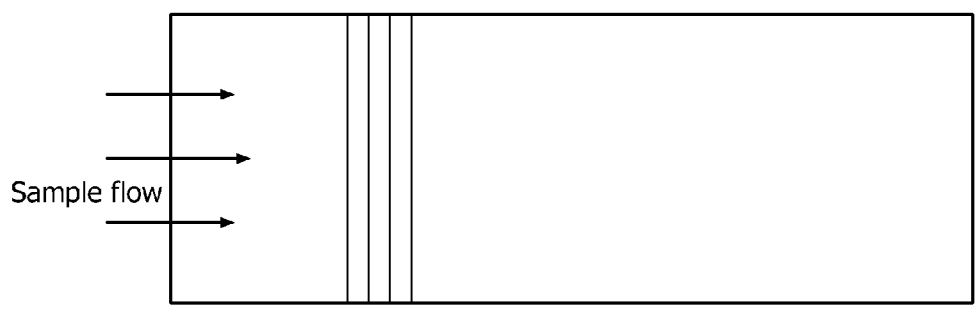
FIG. 9: Schematic drawing of a microarray layout, wherein the probe lines are essentially orthogonal or perpendicular to the sample flow. In this layout the total array surface is best used.
Figure 10:
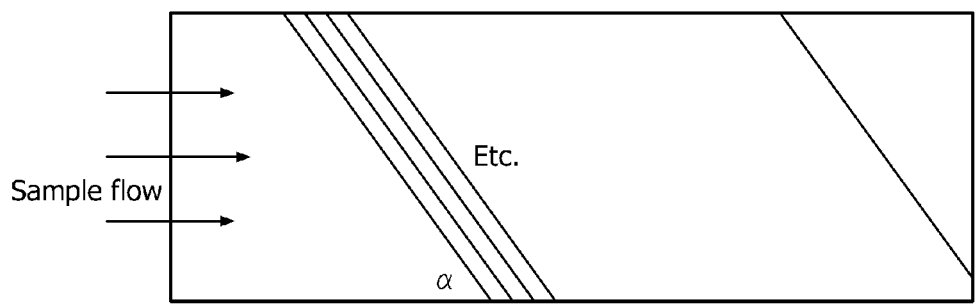
FIG. 10: Schematic drawing of an alternative microarray layout, wherein the probe lines are at an angle α to the sample flow.
Figure 11:
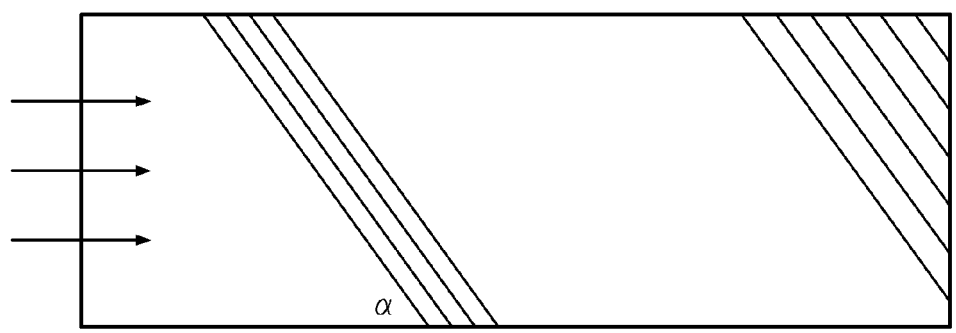
FIG. 11: Schematic drawing of an alternative microarray layout, wherein the probe lines are at an angle α to the sample flow. In this layout lines are also present in the corners, even though they do not span the whole array.
Figure 12:
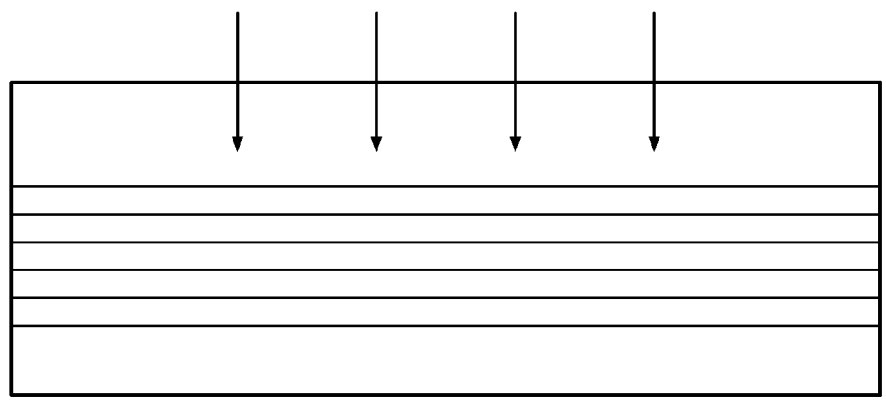
FIG. 12: Schematic drawing of an alternative microarray layout, wherein the probe lines are arranged essentially orthogonal or perpendicular to the sample flow from the wide side of an array

FIG. 8 shows the resulting fluorescence pattern after incubation under the same conditions as for FIG. 7 except for temperature setting, where 50° C. was used instead of 95° C. in the middle section. Under these conditions no denaturing takes place so that the binding efficiency is not increased and the fluorescence intensities remain low.

Example 2

Hybridization tests were performed on amino silane microarray slides (Genorama) with PCR products (114 bp) labeled by Atto 700 under flow conditions (6 µl/min) in microchannels and controlled temperature for 30 minutes in SSC 3× buffer supplemented with 0.1% SDS.

After hybridization microchannels were washed for 5 minutes in SSC buffer with 0.2% SDS to reduce non specific binding.

The fluorescence intensity on capture spots and reference spots was measured by confocal scanner; the signal from capture spots was background subtracted and normalized to the intensity of the reference spots.

Figure 13A:
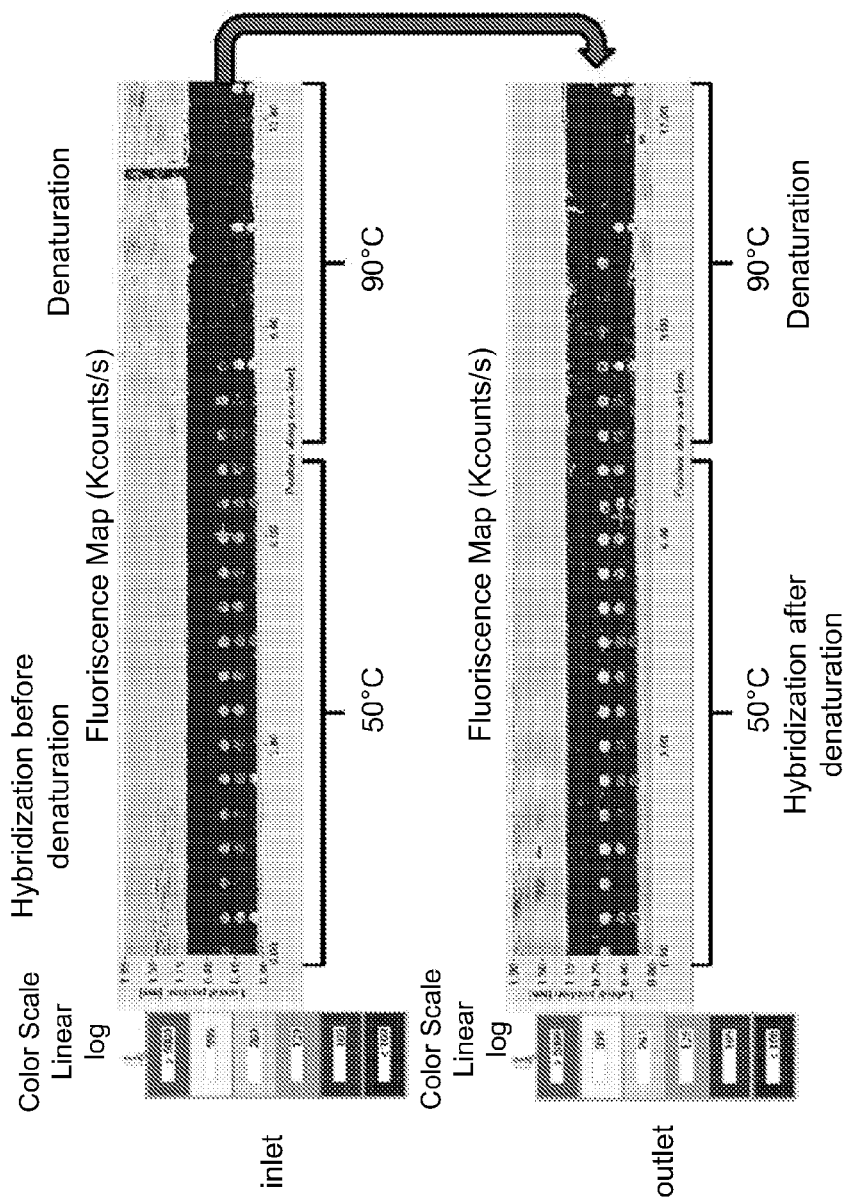
FIG. 13: Hybridization efficiency increase by device according to present invention
Figure 13B:
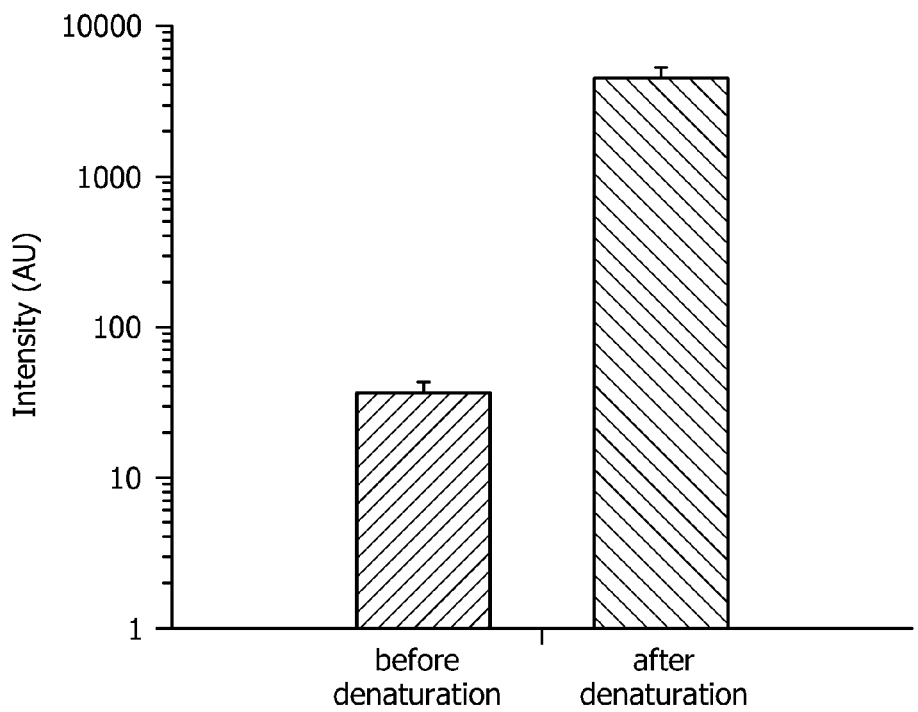
Figure 13C:
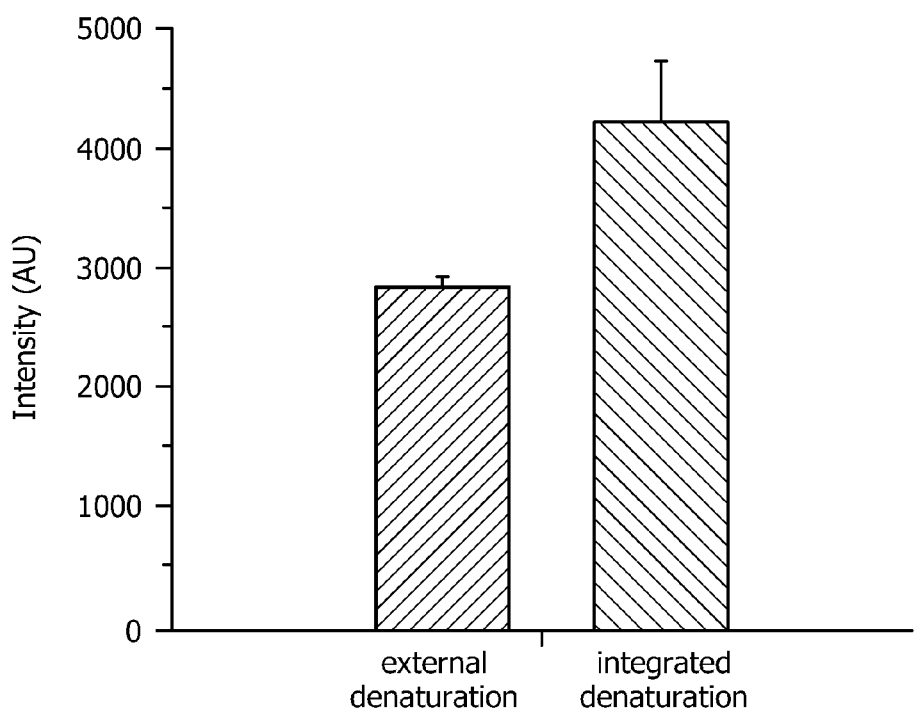

FIG. 13 represents the gain in hybridization efficiency obtained by integrated denaturation under flow conditions in the hybridization channels:

(A) in this experimental setup the sample flows in a 100 µm channel from the inlet to the first hybridization step, maintained at 50° C.; after flowing throw the denaturation zone at 90° C., the sample is introduced in the second hybridization zone, where hybridization occurs at 50° C. with higher efficiency, and finally exit trough the outlet.

(B) the graph refers to the upper row of capture spots in (A); the fluorescence signal is increased by factor 100 when hybridization occurs upon integrated denaturation.

(C) Gain in hybridization efficiency obtained by integrated denaturation in the hybridization channel device: integrated denaturation increases the fluorescence signal intensity by 150% compared to the hybridization signal produced by samples injected in the device after an external denaturation step of 10 minutes at 95° C.

The invention claimed is:

1. A device for the specific selection of target molecules, comprising:
    at least one reaction zone comprising a microarray, wherein the microarray comprises a substrate, on which substrate one or more species of capture molecules are immobilized, wherein the target molecules interact with the capture molecules in the reaction zone, the reaction zone further comprising one or more temperature regulating units for regulating the temperature within the reaction zone;
    at least one non-bound zone, wherein non-bound target molecules that did not interact with the capture molecules are reactivated in the non-bound zone, the non-bound zone comprising one or more temperature regulating units for regulating the temperature within the non-bound zone
    a fluid connection region, in which the reaction zone is in fluid connection with the non-bound zone;
    at least one pump for pumping a fluid through the fluid connection region and between said reaction zone and said non-bound zone, wherein the fluid carries the non-bound target molecules;
    mixing structures in the fluid connection region for mixing the fluid;
    wherein the reaction zone, the non-bound zone and the pump are arranged in a closed loop so that fluid is pumped between the reaction zone and the non-bound zone; and
    wherein the non-bound zone comprises a meandering flow path, wherein at least 40% of the device comprises the meandering flow path, and wherein the meandering flow path has a bifurcation leading to an internal loop having a pump for repetitive passing of the fluid through the meandering flow path.

2. The device of claim 1, wherein the one or more temperature regulating units in the non-bound zone are integrated in the non-bound zone.

3. The device of claim 1, wherein the reaction zone is a hybridizing zone for hybridization of nucleic acids to said capture molecules.

4. The device of claim 1, wherein the non-bound zone is a denaturation zone for mediating denaturation of nucleic acids.

5. The device of claim 1, wherein said immobilized capture molecules are organized in the microarray in the form of spots, elongated spots or lines.

6. The device of claim 5, wherein said lines are arranged in an angle of between about 20° and 90° with respect to the flow path.

7. The device of claim 5, wherein said lines have a width of between about 300 nm and 30 μm and/or are arranged in an inter-line distance of about 500 nm to 100 μm.

8. The device of claim 1, wherein said capture molecules are molecules selected from the group comprising nucleic acids, peptides, proteins, antigens, antibodies, carbohydrates and/or analogs thereof.

* * * * *